(12) United States Patent
Daris et al.

(10) Patent No.: US 10,202,616 B2
(45) Date of Patent: Feb. 12, 2019

(54) PROMOTER AND REGULATORY ELEMENTS FOR IMPROVED EXPRESSION OF HETEROLOGOUS GENES IN HOST CELLS

(71) Applicant: AMGEN INC., Thousand Oaks, CA (US)

(72) Inventors: Mark Daris, Newbury Park, CA (US); Jennitte LeAnn Stevens, Thousand Oaks, CA (US); Chi-Ming Kevin Li, Thousand Oaks, CA (US); Huanying Ge, Cary, NC (US)

(73) Assignee: AMGEN INC., Thousand Oaks, CA (US)

( * ) Notice: Subject to any disclaimer, the term of this patent is extended or adjusted under 35 U.S.C. 154(b) by 0 days.

(21) Appl. No.: 15/519,820

(22) PCT Filed: Oct. 14, 2015

(86) PCT No.: PCT/US2015/055549
§ 371 (c)(1),
(2) Date: Apr. 17, 2017

(87) PCT Pub. No.: WO2016/061240
PCT Pub. Date: Apr. 21, 2016

(65) Prior Publication Data
US 2017/0253889 A1    Sep. 7, 2017

Related U.S. Application Data

(60) Provisional application No. 62/064,335, filed on Oct. 15, 2014.

(51) Int. Cl.
| | |
|---|---|
| *C12N 15/85* | (2006.01) |
| *C12N 9/88* | (2006.01) |
| *C12N 9/02* | (2006.01) |
| *C07K 14/47* | (2006.01) |

(52) U.S. Cl.
CPC .............. *C12N 15/85* (2013.01); *C07K 14/47* (2013.01); *C12N 9/0008* (2013.01); *C12N 9/88* (2013.01); *C12Y 102/01012* (2013.01); *C12N 2830/15* (2013.01); *C12N 2830/34* (2013.01); *C12N 2830/42* (2013.01); *C12N 2830/85* (2013.01)

(58) Field of Classification Search
CPC ............ C12N 2830/15; C12N 2830/40; C12N 2830/46
See application file for complete search history.

(56) References Cited

U.S. PATENT DOCUMENTS

| | | |
|---|---|---|
| RE30,985 E | 6/1982 | Cartaya |
| 4,560,655 A | 12/1985 | Baker |
| 4,657,866 A | 4/1987 | Kumar |
| 4,767,704 A | 8/1988 | Cleveland et al. |
| 4,927,762 A | 5/1990 | Darfler |
| 5,122,469 A | 6/1992 | Mather et al. |
| 5,229,275 A | 7/1993 | Goroff |
| 5,302,697 A | 4/1994 | Goodey et al. |
| 5,545,403 A | 8/1996 | Page |
| 5,545,807 A | 8/1996 | Surani et al. |
| 5,565,332 A | 10/1996 | Hoogenboom et al. |
| 5,567,610 A | 10/1996 | Borrebaeck et al. |
| 5,573,905 A | 11/1996 | Lerner et al. |
| 5,589,369 A | 12/1996 | Seidman et al. |
| 5,591,669 A | 1/1997 | Krimpenfort et al. |
| 5,633,162 A | 5/1997 | Keen et al. |
| 5,877,293 A | 3/1999 | Adair et al. |
| 5,939,598 A | 8/1999 | Kucherlapati et al. |
| 6,022,952 A | 2/2000 | Weiner et al. |
| 6,054,287 A | 4/2000 | Gao et al. |
| 6,210,924 B1 | 4/2001 | Hu et al. |
| 6,331,415 B1 | 12/2001 | Cabilly et al. |
| 6,335,178 B1 | 1/2002 | Weiner et al. |
| 7,029,090 B2 | 4/2006 | Nishida et al. |
| 2002/0004215 A1 | 1/2002 | Osbourn et al. |
| 2002/0199213 A1 | 12/2002 | Tomizuka et al. |
| 2003/0044772 A1 | 3/2003 | Watkins et al. |
| 2003/0092125 A1 | 5/2003 | Davis et al. |
| 2003/0104400 A1 | 6/2003 | Ruben et al. |
| 2003/0190317 A1 | 10/2003 | Baca et al. |
| 2013/0344604 A1* | 12/2013 | Aebischer-Gumy ..................... C12N 15/79 435/455 |

FOREIGN PATENT DOCUMENTS

| | | |
|---|---|---|
| EP | 0 481 790 A2 | 4/1992 |
| WO | 87/00195 A1 | 1/1987 |
| WO | 90/003430 A1 | 4/1990 |
| WO | 91/10741 A1 | 7/1991 |
| WO | 91/17271 A1 | 11/1991 |
| WO | 92/01047 A1 | 1/1992 |
| WO | 94/02602 A1 | 2/1994 |
| WO | 96/30498 A1 | 10/1996 |
| WO | 96/33735 A1 | 10/1996 |
| WO | 98/24893 A2 | 6/1998 |

(Continued)

OTHER PUBLICATIONS

GenBank Accession No. NW_003613610.1, publicly available Oct. 2011, printed as pp. 1/39-39-39. (Year: 2011).*
Cartharius et al. MatInspector and beyond: promoter analysis based on transcription factor binding sites. Bioinformatics, vol. 21, No. 13, pp. 2933-2942, 2005 (Year: 2005).*
Baeuerle, P. A. et al., "BiTE: Teaching antibodies to engage T-cells for cancer therapy," *Curr Opin Mol Ther.*, 11(1):22-30 (2009).
Barnes et al., "Methods for Growth of Cultured Cells in Serum-Free Medium," *Anal. Biochem.*, 102:255-270 (1980).
Berger and Kimmel, eds., *Methods in Enzymology: Guide to Molecular Cloning Techniques*, vol. 152, Academic Press, Inc., San Diego, CA (1987).(Table of Contents Only).

(Continued)

*Primary Examiner* — Jennifer Ann Dunston
(74) *Attorney, Agent, or Firm* — Jonathan M. Dermott

(57) ABSTRACT

Disclosed are a recombinant expression vector and a host cell that contains the vector.

10 Claims, 9 Drawing Sheets

Specification includes a Sequence Listing.

(56) References Cited

FOREIGN PATENT DOCUMENTS

| WO | 00/24782 A2 | 5/2000 |
|---|---|---|
| WO | 2006/123097 A2 | 11/2006 |
| WO | 2007/045463 A1 | 4/2007 |
| WO | 2008/085962 A2 | 7/2008 |
| WO | 2013/084157 A1 | 6/2013 |

OTHER PUBLICATIONS

Bhatnagar, P. K. et al., "Structure-activity relationships of novel hematoregulatory peptides," *J. Med. Chem.*, 39(19):3814-3819 (1996).
Boulianne, G. L. et al., "Production of functional chimaeric mouse/human antibody," *Nature*, 312:643-646 (1984).
Brodeur et al., *Monoclonal Antibody Production Techniques and Applications*, Marcel Dekker, Inc. New York, pp. 51-63 (1987).
Bruggermann et al., "Designer Mice: The Production of Human Antibody Repertoires in Transgenic Animals," *Generation of Antibodies by Cell and Gene Immortalization, Year in Immuno.*, Basel, Karger, 7:33-40 (1993).
Burton, D. R., and Barbas III, C. F., "Human Antibodies from Combinatorial Libraries," *Adv. Immunol.*, 57:191-280 (1994).
Caton, A. J. and Koprowski, H., "Influenza virus hemagglutinin-specific antibodies isolated from a combinatorial expression library are closely related to the immune response of the donor," *Proc. Natl. Acad. Sci. USA*, 87:6450-6454 (1990).
Chu, G. et al., "SV40 DNA transfection of cells in suspension: analysis of the efficiency of transcription and translation of T-antigen," *Gene*, 13:197-202 (1981).
Chung, J. H. et al., "A 5' element of the chicken beta-globin domain serves as an insulator in human erythroid cells and protects against position effect in *Drosophila*," *Cell.*, 74(3):505-514 (1993).
Clackson, T. and Wells, J. A., "In vitro selection from protein and peptide libraries," *TIBTECH*, 12:173-184 (1994).
Co, M. S. et al., "A Humanized Antibody Specific for the Platelet Integrin gpIIb/IIIa," *J. Immunol.*, 152:2968-2976 (1994).
Cuthbertson, A. S. et al., "Design of Low Molecular Weight Hematoregulatory Agents from the Structure-Activity Relationship of a Dimeric Pentapeptide," *J. Med. Chem.*, 40:2876-2882 (1997).
Davis et al., "*Methods in Molecular Biology*," Elsevier New York Amsterdam, London (1986) (Table of Contents Only).
Engels et al., "Gene Synthesis," *Angew. Chem. Int. Ed. Engl.*, 28:716-734 (1989).
Ferrari, S. et al., "Chromatin domains boundaries delimited by a histone binding protein in yeast," *J. Biol. Chem.*, 279(53):55520-55530 (2004).
Gleason, M. K. et al., Bispecific and trispecific killer cell engagers directly activate human NK cells through CD16 signaling and induce cytotoxicity and cytokind production, *Mol. Cancer Ther.*, 11(12):2674-2684 (2012).
Goding, *Monoclonal Antibodies: Principles and Practice:* Production and application of monoclonal antibodies in cell biology, biochemistry, and immunology, Academic Press, Chapter 3, pp. 59-103 (1986).
Goeddel, D. V. et al., Editor, "Systems for Heterologous Gene Expression," *Methods Enzymol., Gene Expression Technology*, Academic Press, Inc., Harcourt Brace Jovanovich, Publishers, San Diego, CA, Section 1, Chapter 1, Introduction, 185:3-7 (1990).
Graham, F. L. et al., "Characteristics of a Human Cell Line Transformed by DNA from Human Adenovirus Type 5," *J. Gen. Virol.*, 36:59-72 (1977).
Graham, F. L. et al., "A New Technique for the Assay of Infectivity of Human Adenovirus 5 DNA," *Virology*, 52:456-467 (1973).
Guss et al., "Structure of the IgG-binding regions of streptococcal protein G," *EMBO J.*, 5(7):1567-1575 (1986).
Ham, R. G. et al., "Media and Growth Requirements," *Meth. Enz.*, 58:44-93 (1979).
Hoogenboom et al., "By-passing Immunisation Human Antibodies from Synthetic Repertoires of Germline $V_H$ Gene Segments Rearranged in Vitro," *J. Mol. Biol.*, 227:381-388 (1992).

Jakobovits, A. et al., "Germ-line transmission and expression of a human-derived yeast artificial chromosome," *Nature*, 362:255-258 (1993).
Jakobovits, A. et al., "Analysis of homozygous mutant chimeric mice: Deletion of the immunoglobulin heavy-chain joining region blocks B-cell development and antibody production," *Proc. Natl. Acad. Sci. USA*, 90:2551-2555 (1993).
Jespers, L. S. et al., "Guiding the Selection of Human Antibodies from Phage Display Repertoires to a Single Epitope of an Antigen," *Bio/Technology*, 12:899-903 (1994).
Jones et al., "Replacing the complementarity-determining regions in a human antibody with those from a mouse," *Nature*, 321:522-525 (1986).
Kwaks, T. H. J. et al., "Identification of anti-repressor elements that confer high and stable protein production in mammalian cells," *Nature Biotechnology, Nature Publishing Group*, US, 21(5):553-558 (2003).
Kellum, R. et al., "A group of scs elements function as domain boundaries in an enchancer-blocking assay," *Mol. Cell Biol.*, 12(5):2424-2431 (1992).
Kettleborough, C. A. et al., "Humanization of a mouse monoclonal antibody by CDR-grafting the importance of framework residues on loop conformation," *Protein Eng.*, 4(7):773-783 (1991).
Kilpatrick, K. E. et al., "Rapid development of affinity matured monoclonal antibodies using RIMMS," *Hybridoma*, 16(4):381-389 (1997).
Kohler et al., "Continuous cultures of fused cells secreting antibody of predefined specificity," *Nature*, 256:495-497 (1975).
Kozbor, D. et al. "A Human Hybrid Myeloma for Production of Human Monoclonal Antibodies," *J. Immunol.*, 133(6):3001-3005 (1984).
Le Fourn, V. et al., "CHO cell engineering to prevent polypeptide aggregation and improve therGapeutic protein secretion," *Metabolic Engineering*, 21:91-102 (2014).
Li, B. et al., "The role of chromatin during transcription," *Cell*, 128:707-719 (2007).
Lindmark, R. et al., "Binding of Immunoglobulins to Protein A and Immunoglobulin Levels in Mammalian Sera," *J. of Immunol. Meth.*, 62:1-13 (1983).
Lowman, "Bacteriophase Display and Discovery of Peptide Leads for Drug Development," *Ann. Rev. Biophys. Biomol. Struct.*, 26:401-424 (1997).
Magnusson et al., "Sustained, high transgene expression in liver with plasmid vectors using optimized promoter-enhancer combinations," *Journal of Gene Medicine*, 13(7-8):382-391 (2011).
Maniatis, T. et al., "Vectors That Express Cloned DNA in *Escherichia coli*," *Molecular Cloning. A Laboratory Manual. Cold Spring Harbor Laboratory*, Cold Spring Harbor, NY, Chapter 12, pp. 412-423, (1982).
Maniatis, T. et al., "Regulation of Inducible and Tissue-Specific Gene Expression," *Science*, 236:1237-1244 (1987).
Marino, M. H., "Expression systems for heterologous protein production," *Bio Pharm.*, 2:18-33 (1989).
Marks, J. D. et al., "By-passing Immunization: Human Antibodies from V-gene Libraries Displayed on Phage," *J. Mol. Biol.*, 222:581-597 (1991).
Mather, J. P. et al., Culture of Testicular Cells in Hormone-Supplemented Serum-Free Medium, *Annals NY Acad. Sci.*, 383:44-68 (1982).
Mather, J. P. et al., "Establishment and Characterization of Two Distinct Mouse Testicular Epithelial Cell Lines," *Biol. Reprod.*, 23:243-252 (1980).
Mendez, M. J. et al., "Functional transplant of megabase human immunoglobulin loci recapitulates human antibody response in mice," *Nat. Genet.*, 15:146-156 (1997).
Morrison, S. L. et al., "Chimeric Human Antibody Molecules; Mouse Antigen Binding Domains with Human Constant Region Domains," *Proc. Natl. Acad. Sci. USA*, 81:6851-6855 (1984).
Morrison, S. L. and Oi, V. T., "Genetically Engineered Antibody Molecules," *Adv. Immunol.*, 44:65-92 (1988).
Munson, P. J. et al., "LIGAND: A versatile computerized approach for characterization of ligand-binding systems," *Anal. Biochem.*, 107:220-239 (1980).

(56) References Cited

OTHER PUBLICATIONS

NCBI Reference Sequence NW_003613610.1, Hamster GAPDH Promoter Sequence from Gene ID: 100736557; (May 2016) downloaded from: https://www.ncbi.nlm.nih.gov/nuccore/NW_003613610.1?from=3572132&to=3575848&report=genbank on Sep. 29, 2017.

Otte, A. P. et al., "Various expression-augmenting DNA elements benefit from STAR-Select, a novel high stringency selection system for protein expression," *Biotechnol. Prog.,* 23(4):801-807 (2007).

Padlan, E. A., "Anatomy of the Antibody Molecule," *Molecular Immunol.,* 31(3):169-217 (1994).

Padlan, E. A., "A Possible Procedure for Reducing the Immunolgenicity of Antibody Variable Domains While Preserving Their Ligand-Binding Properties," *Molecular Immunol.,* 28(4/5):489-498 (1991).

Pikaart, M. J., "Loss of transcriptional activity of a transgene is accompanied by DNA methylation and histone deacetylation and is prevented by insulators," *Genes Dev.,* 12:2852-2862 (1998).

Rathanaswami, P. et al., "High-affinity binding measurements of antibodies to cell-surface-expressed antigens," *Analytical Biochemistry,* 373:52-60 (2008).

Sambrook, J. et al., *Molecular Cloning: A Laboratory Manual,* 3rd Edition, vols. 1-3, Cold Spring Harbor Laboratory Press, Cold Spring Harbor, NY (2001) (Table of Contents Only).

Sambrook, J. et al., *Molecular Cloning: A Laboratory Manual,* 2nd Edition, Books 1-3, Cold Spring Harbor Laboratory Press, Cold Spring Harbor, NY (1989) (Table of Contents Only).

Sanger, F. et al., "DNA sequencing with chain-terminating inhibitors," *Proc. Natl. Acad. Sci. USA,* 74(12):5463-5467 (1977).

Studnicka, G. M. et al., "Human-engineering monoclonal antibodies retain full specific binding activity by preserving non-CDR complementarity-modulating residues," *Protein Engineering,* 7(6):805-814 (1994).

Urlaub, G. et al., "Isolation of Chinese hamster cell mutants deficient in dihydrofolate reductase activity," *Proc. Natl. Acad. Sci. USA,* 77(7):4216-4220 (1980).

Verhoeyen, M. et al., "Reshaping Human Antibodies: Grafting an Antilysozyme Activity," *Science,* 239:1534-1536 (1988).

Voss, S. D. et al., "The role of enhancers in the regulation of cell-type-specific transcriptional control," *Trends Biochem. Sci.,* 11:287-289 (1986).

Watkins, J. D. et al., "Screening of Phage-Expressed Antibody Libraries by Capture Lift," *Methods in Molecular Biology, Antibody Phage Display: Methods and Protocols,* O'Brien,.P. M. and Aitken, R., Eds., University of Glasgow, Glasgow, Scotland, UK, Humana Press, Totowa, NJ, Chapter 14, 178:187-193 (2002).

Wells, J. A. et al., "Cassette mutagenesis: an efficient method for generation of multiple mutations at defined sites," *Gene,* 34(2-3):315-323 (1985).

Williams, S. et al., "CpG Island fragments from HNRAP2B1/CBX3 genomic locus reduce silencing and enhance transgene expression from the hCMV promoter/enhance in mammalian cells," *BMC Biotechnol.,* Biomed Central Ltd., London, GB 5(1):17 (2005).

Winter, G., et al., "Making Antibodies by Phage Display Technology," *Annu. Rev. Immunol.,* 12:433-455 (1994).

Wurm, F. and Bernard, A., "Large-scale transient expression in mammalian cells for recombinant protein production," *Curr. Opin. Biotechnol.,* 10(2):156-159 (1999).

Xu, M. et al., "Optimization of transcriptional regulatory elements for constructing plasmid vectors," *Gene,* 272(1):149-156 (2001).

\* cited by examiner

PROMOTER AND REGULATORY ELEMENTS FOR IMPROVED EXPRESSION OF HETEROLOGOUS GENES IN HOST CELLS

This application is a national stage application under 35 U.S.C. § 371 of International Application No. PCT/US2015/055549, having an international filing date of Oct. 14, 2015, which claims the benefit of U.S. Provisional Patent Application No. 62/064,335, filed Oct. 15, 2014, each of which is incorporated herein by reference in its entirety.

The instant application contains an ASCII "txt" compliant sequence listing submitted via EFS-WEB on Apr. 17, 2017, which serves as both the computer readable form (CRF) and the paper copy required by 37 C.F.R. Section 1.821(c) and 1.821(e), and is hereby incorporated by reference in its entirety. The name of the "txt" file created on Apr. 6, 2017, is: A-1917-US-PCT_FinalSeqList040617_ST25.txt, and is 28 kb in size.

Throughout this application various publications are referenced within parentheses or brackets. The disclosures of these publications in their entireties are hereby incorporated by reference in this application in order to more fully describe the state of the art to which this invention pertains.

BACKGROUND OF THE INVENTION

1. Field of the Invention

The present invention is directed to the field of recombinant gene expression.

2. Discussion of the Related Art

There is a great demand for biologic molecules such as proteins, and particularly antibodies or antibody fragments, e.g., biologics that include the immunoglobulin Fc region.

Expression systems for the production of recombinant polypeptides are well-known in the state of the art and are described by, e.g., Marino M H (1989) Biopharm, 2: 18-33; Goeddel D V et al. (1990) Methods Enzymol 185: 3-7; Wurm F & Bernard A (1999) Curr Opin Biotechnol 10: 156-159. Polypeptides for use in pharmaceutical applications are preferably produced in mammalian cells such as Chinese Hamster Ovary (CHO) cells, NS0 cells, SP2/0 cells, COS cells, HEK cells, BHK cells, or the like. Various CHO-derived cell lines are particularly well-suited for industrial production of many different therapeutic biologic molecules. (E.g., Hu et al., U.S. Pat. No. 6,210,924 B1).

The essential elements of an expression vector used for this purpose are normally selected from a prokaryotic plasmid propagation unit, for example *E. coli*, comprising a prokaryotic origin of replication and a prokaryotic selection marker, optionally a eukaryotic selection marker, and one or more expression cassettes for the expression of the structural gene(s) of interest each comprising a promoter, a polynucleotide sequence encoding a polypeptide, and optionally a transcription terminator including a polyadenylation signal. For transient expression in mammalian cells a mammalian origin of replication, such as the SV40 Ori or OriP, can be included. As promoter a constitutive or inducible promoter can be selected. For optimized transcription a Kozak sequence may be included in the 5' untranslated region. For mRNA processing, in particular mRNA splicing and transcription termination, mRNA splicing signals, depending on the organization of the structural gene (exon/intron organization), may be included as well as a polyadenylation signal. Expression of a gene is performed either in transient or using a stable cell line. However, the level of stable and high expression of a polypeptide in a production cell line is crucial to the overall process of the industrial production of recombinant polypeptides.

High cost and relatively poor yield have been limiting factors in the availability of biologic molecules and it has been a major challenge to develop robust processes that stably increase the yield of desirable biological molecules on an industrial scale. These and other benefits the present invention provides.

SUMMARY OF THE INVENTION

The present invention involves a recombinant expression vector, comprising an expression cassette comprising a hamster glyceraldehyde-3-phosphate dehydrogenase (GAPDH) (EC 1.2.1.12; GAPDH) promoter, operably linked to an exogenous gene of interest. The expression vector also includes an regulatory element that (a) comprises a nucleic acid sequence that is at least 95%, at least 96%, at least 97%, at least 98%, at least 99%, or 100% identical to SEQ ID NO:35, or at least 95%, at least 96%, at least 97%, at least 98%, at least 99%, or 100% identical to SEQ ID NO:38; and (b) is operably linked to the promoter. The regulatory element sequences SEQ ID NOS; 35 and 38 are not naturally found on the same hamster chromosome as the GAPDH promoter sequence.

In some useful embodiments of the recombinant expression vector, the regulatory element in the plus orientation. In other useful embodiments the regulatory element is in the minus orientation.

The present invention is also directed to a mammalian host cell containing the expression vector, for example, a Chinese Hamster Ovary (CHO) cell.

The present invention is particularly useful for creating cell lines intended for industrial production of biologics, such as antigen binding proteins, hormones, or other therapeutic peptides, a setting in which stable and high yield recombinant expression of exogenous proteins is needed.

This and other benefits will be further described hereinbelow.

Conditioned medium (CM) was harvested 6 days later. Titers of human Fc protein in CM (reported as mg/L) were determined by ForteBIO OCTET® Red and ranges are shown from triplicate transfections.

Figure 6:
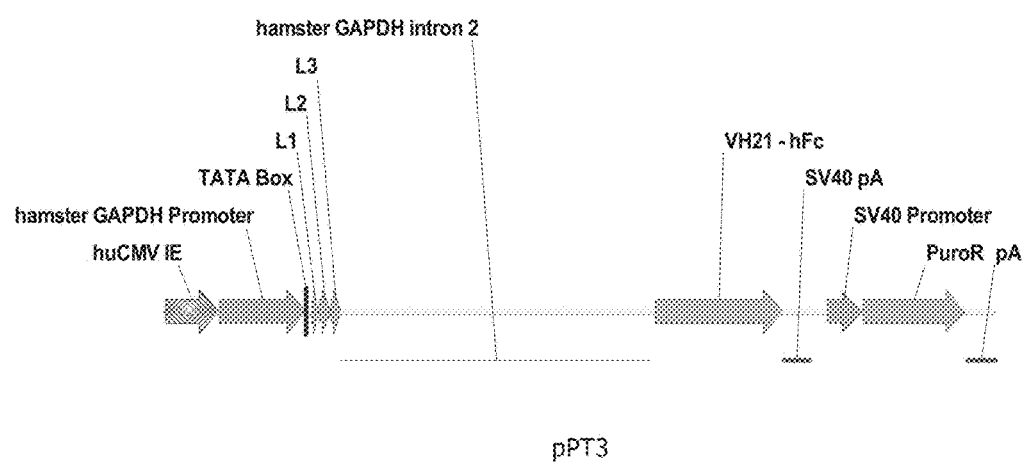

FIG. 6 is a schematic representation of the expression cassettes contained on the pPT3 stable expression vector. Not shown is the vector backbone which contains sequences which do not impact the results presented here.

Figure 7:
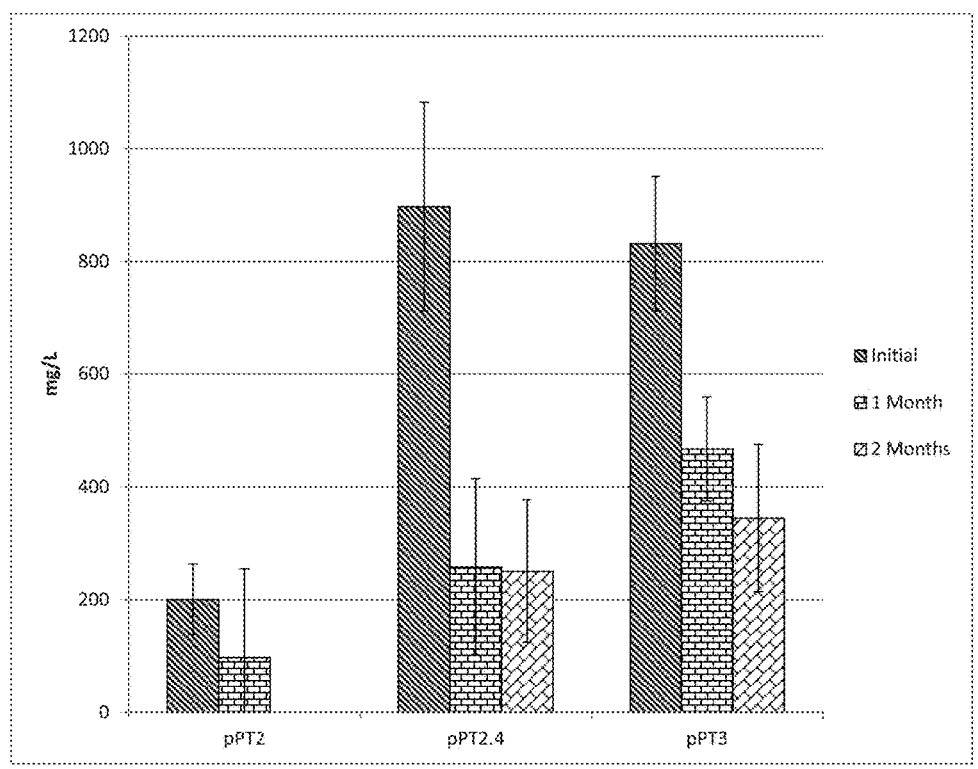

FIG. 7 shows CHO-S stable expression pools derived from transfection and selection with pPT2, pPT2.4, and pPT3. Recovered pools were maintained in culture for the following time points: right after recovery from selection (initial); one month and 2 months post selection. Cells were then seeded at 1E6 cells/ml in a 24 well deep well plate. Conditioned medium was harvested 6 days later and titers determined by ForteBIO OCTET® Red. The results bars for each vector indicated on the x-axis are set forth left-to-right at the following time points: initial, 1 month, and 2 months.

Figure 8:
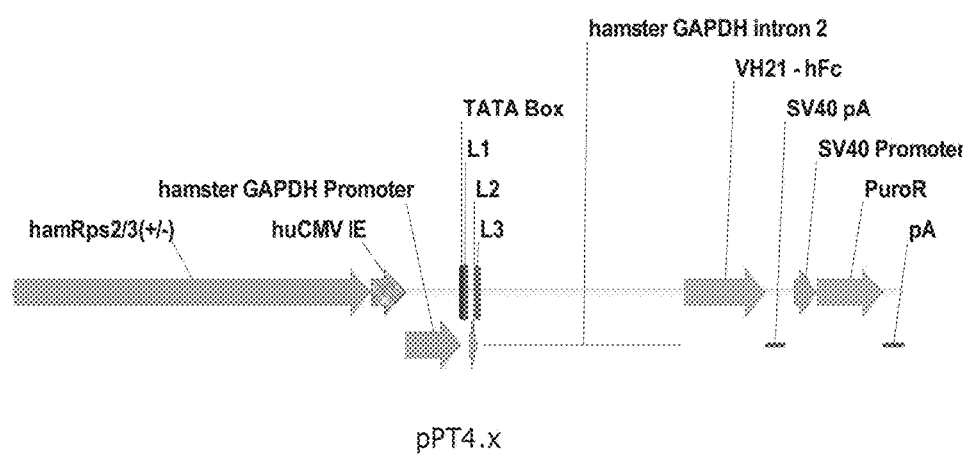

FIG. 8 is a schematic representation of the expression cassettes contained on the pPT4.x stable expression vector. Not shown is the vector backbone which contains sequences which do not impact the results presented here.

Figure 9:
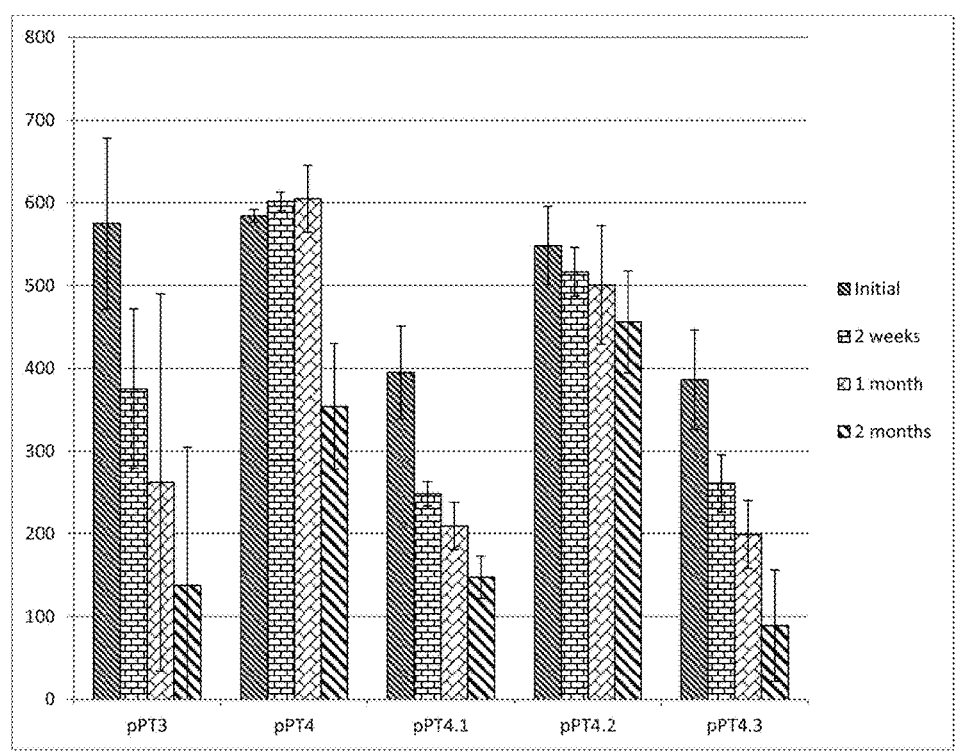

FIG. 9 shows CHO-S stable expression pools derived from transfection and selection with, pPT3, pPT4, pPT4.1, pPT4.2, pPT4.3 Recovered pools were maintained in culture for the following time points: right after recovery from selection (initial); one month and 2 months post selection. Cells were then seeded at 1E6 cells/mL in a 24 well deep well plate. Conditioned medium was harvested 6 days later and titers determined by ForteBIO OCTET® Red. The results bars for each vector indicated on the x-axis are set forth left-to-right at the following time points: initial, 2 weeks, 1 month, and 2 months.

DETAILED DESCRIPTION OF EMBODIMENTS

The section headings used herein are for organizational purposes only and are not to be construed as limiting the subject matter described.

Definitions

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular. Thus, as used in this specification and the appended claims, the singular forms "a", "an" and "the" include plural referents unless the context clearly indicates otherwise. For example, reference to "a protein" includes a plurality of proteins; reference to "a cell" includes populations of a plurality of cells. References to "yEx" mean, and are used interchangeably with, "y×10$^z$", where y is a number multiplied by a certain exponent of 10, and z is the exponent, for example "1E6" equals $1\times10^6$, or "5E6" equals $5\times10^6$, or "5E-6" equals $5\times10^{-6}$.

"Mammal" refers to any animal classified as a mammal, including humans, domestic and farm animals, and zoo, sports, or pet animals, such as dogs, horses, cats, cows, rodents (e.g., rats, mice, guinea pigs, hamsters), rabbits, pigs, sheep, goats, primates (e.g., monkeys, apes), etc. A "non-human" mammal is a mammal other than a human. A mammalian cell is a cell originally derived from a mammal.

As used herein, the terms "cell culture medium" and "culture medium" refer to a nutrient solution used for growing mammalian cells in vitro that typically provides at least one component from one or more of the following categories: 1) an energy source, usually in the form of a carbohydrate such as, for example, glucose; 2) one or more of all essential amino acids, and usually the basic set of twenty amino acids plus cysteine; 3) vitamins and/or other organic compounds required at low concentrations; 4) free fatty acids; and 5) trace elements, where trace elements are defined as inorganic compounds or naturally occurring elements that are typically required at very low concentrations, usually in the micromolar range. The nutrient solution may optionally be supplemented with additional components to optimize growth, reprogramming and/or differentiation of cells.

The mammalian cell culture within the present invention is prepared in a medium suitable for the particular cell being cultured. Suitable cell culture media that may be used for culturing a particular cell type would be apparent to one of ordinary skill in the art. Exemplary commercially available media include, for example, Ham's F10 (SIGMA), Minimal Essential Medium (MEM, SIGMA), RPMI-1640 (SIGMA), Dulbecco's Modified Eagle's Medium (DMEM, SIGMA), and DMEM/F12 (Invitrogen). Any of these or other suitable media may be supplemented as necessary with hormones and/or other growth factors (such as but not limited to insulin, transferrin, or epidermal growth factor), salts (such as sodium chloride, calcium, magnesium, and phosphate), buffers (such as HEPES), nucleosides (such as adenosine and thymidine), antibiotics (such as puromycin, neomycin, hygromycin, blasticidin, or Gentamycin™), trace elements (defined as inorganic compounds usually present at final concentrations in the micromolar range) lipids (such as linoleic or other fatty acids) and their suitable carriers, and glucose or an equivalent energy source, and/or modified as described herein to facilitate production of recombinant glycoproteins having low-mannose content. In particular embodiments, the cell culture medium is serum-free.

When defined medium that is serum-free and/or peptone-free is used, the medium is usually enriched for particular amino acids, vitamins and/or trace elements (see, for example, U.S. Pat. No. 5,122,469 to Mather et al., and U.S. Pat. No. 5,633,162 to Keen et al.). Depending upon the requirements of the particular cell line used or method, culture medium can contain a serum additive such as Fetal Bovine Serum, or a serum replacement. Examples of serum-replacements (for serum-free growth of cells) are TCH™, TM-235™, and TCH™; these products are available commercially from Celox (St. Paul, Minn.), and KOSR (knock-out (KO) serum replacement; Invitrogen).

In the methods and compositions of the invention, cells can be grown in serum-free, protein-free, growth factor-free, and/or peptone-free media. The term "serum-free" as applied to media in general includes any mammalian cell culture medium that does not contain serum, such as fetal bovine serum (FBS). The term "insulin-free" as applied to media includes any medium to which no exogenous insulin has been added. By exogenous is meant, in this context, other than that produced by the culturing of the cells themselves. The term "growth-factor free" as applied to media includes any medium to which no exogenous growth factor (e.g., insulin, IGF-1) has been added. The term "peptone-free" as applied to media includes any medium to which no exogenous protein hydrolysates have been added such as, for example, animal and/or plant protein hydrolysates.

Optimally, for purposes of the present invention, the culture medium used is serum-free, or essentially serum-free unless serum is required by the inventive methods or for the growth or maintenance of a particular cell type or cell line. By "serum-free", it is understood that the concentration of serum in the medium is preferably less than 0.1% (v/v) serum and more preferably less than 0.01% (v/v) serum. By "essentially serum-free" is meant that less than about 2% (v/v) serum is present, more preferably less than about 1% serum is present, still more preferably less than about 0.5% (v/v) serum is present, yet still more preferably less than about 0.1% (v/v) serum is present.

"Culturing" or "incubating" (used interchangeably with respect to the growth, reprogramming, differentiation, and/or maintenance of cells or cell lines) is under conditions of sterility, temperature, pH, atmospheric gas content (e.g., oxygen, carbon dioxide, dinitrogen), humidity, culture container, culture volume, passaging, motion, and other parameters suitable for the intended purpose and conventionally known in the art of mammalian cell culture.

"Polypeptide" and "protein", or "proteinaceous molecule" are used interchangeably herein and include a molecular chain of two or more amino acids linked covalently through peptide bonds. The terms do not refer to a specific length of the product. Thus, "peptides," and "oligopeptides," are included within the definition of polypeptide. The terms include post-translational modifications of the polypeptide, for example, glycosylations, acetylations, phosphorylations and the like. In addition, protein fragments, analogs, mutated or variant proteins, fusion proteins and the like are included within the meaning of polypeptide. The terms also include molecules in which one or more amino acid analogs or non-canonical or unnatural amino acids are included as can be expressed recombinantly using known protein engineering techniques. In addition, fusion proteins can be derivatized as described herein by well-known organic chemistry techniques. The term "fusion protein" indicates that the protein includes polypeptide components derived from more than one parental protein or polypeptide. Typically, a fusion protein is expressed from a fusion gene in which a nucleotide sequence encoding a polypeptide sequence from one protein is appended in frame with, and optionally separated by a linker from, a nucleotide sequence encoding a polypeptide sequence from a different protein. The fusion gene can then be expressed by a recombinant host cell as a single protein.

The term "antigen binding protein" (ABP) includes an antibody or antibody fragment, as defined above, a BiTE® (Bi-specific T-cell engager)(e.g., Baeuerle P A, et al., BiTE: Teaching antibodies to engage T-cells for cancer therapy, *Curr Opin Mol Ther.* 11(1):22-30 (2009)), or a BiKE (Bi-specific killer cell engager)(e.g., Gleason et al., Bispecific and trispecific killer cell engagers directly activate human NK cells through CD16 signaling and induce cytotoxicity and cytokine production, *Mol. Cancer Ther.* 11(12):1-11 (2012)), and recombinant peptides or other compounds that contain sequences derived from CDRs having the desired antigen-binding properties such that they specifically bind a target antigen of interest. The term "antigen" refers to a molecule or a portion of a molecule capable of being bound by a selective binding agent, such as an antigen binding protein (including, e.g., an antibody or immunological functional fragment thereof), and additionally capable of being used in an animal to produce antibodies capable of binding to that antigen. An antigen may possess one or more epitopes that are capable of interacting with different antigen binding proteins, e.g., antibodies. The term "epitope" is the portion of a molecule that is bound by an antigen binding protein (for example, an antibody). The term includes any determinant capable of specifically binding to an antigen binding protein, such as an antibody or to a T-cell receptor. An epitope can be contiguous or non-contiguous (e.g., in a single-chain polypeptide, amino acid residues that are not contiguous to one another in the polypeptide sequence but that within the context of the molecule are bound by the antigen binding protein). In certain embodiments, epitopes may be mimetic in that they comprise a three dimensional structure that is similar to an epitope used to generate the antigen binding protein, yet comprise none or only some of the amino acid residues found in that epitope used to generate the antigen binding protein. Most often, epitopes reside on proteins, but in some instances may reside on other kinds of molecules, such as nucleic acids. Epitope determinants may include chemically active surface groupings of molecules such as amino acids, sugar side chains, phosphoryl or sulfonyl groups, and may have specific three dimensional structural characteristics, and/or specific charge characteristics. Generally, antibodies specific for a particular target antigen will preferentially recognize an epitope on the target antigen in a complex mixture of proteins and/or macromolecules.

The term "antibody" is used in the broadest sense and includes fully assembled antibodies, monoclonal antibodies (including human, humanized or chimeric antibodies), polyclonal antibodies, multispecific antibodies (e.g., bispecific antibodies), and antibody fragments that can bind antigen (e.g., Fab, Fab', F(ab')2, Fv, single chain antibodies, diabodies), comprising complementarity determining regions (CDRs) of the foregoing as long as they exhibit the desired biological activity. Multimers or aggregates of intact molecules and/or fragments, including chemically derivatized antibodies, are contemplated. Antibodies of any isotype class or subclass, including IgG, IgM, IgD, IgA, and IgE, IgG1, IgG2, IgG3, IgG4, IgA1 and IgA2, or any allotype, are contemplated. Different isotypes have different effector functions; for example, IgG1 and IgG3 isotypes typically have antibody-dependent cellular cytotoxicity (ADCC) activity. Glycosylated and unglycosylated antibodies are included within the term "antibody".

In general, an antigen binding protein, e.g., an antibody or antibody fragment, "specifically binds" to an antigen when it has a significantly higher binding affinity for, and consequently is capable of distinguishing, that antigen, compared to its affinity for other unrelated proteins, under similar binding assay conditions. Typically, an antigen binding protein is said to "specifically bind" its target antigen when the equilibrium dissociation constant ($K_d$) is $\leq 10^{-8}$ M. The antibody specifically binds antigen with "high affinity" when the $K_d$ is $\leq 5 \times 10^{-9}$ M, and with "very high affinity" when the $K_d$ is $\leq 5 \times 10^{-10}$ M. In one embodiment, the antibodies will bind to a target of interest with a $K_d$ of between about $10^{-8}$M and $10^{-10}$ M, and in yet another embodiment the antibodies will bind with a $K_d \leq 5 \times 10^{-9}$. In particular embodiments the antigen binding protein, the isolated antigen binding protein specifically binds to a target antigen of interest expressed by a mammalian cell (e.g., CHO, HEK 293, Jurkat), with a $K_d$ of 500 pM ($5.0 \times 10^{-10}$ M) or less, 200 pM ($2.0 \times 10^{-10}$ M) or less, 150 pM ($1.50 \times 10^{-10}$ M) or less, 125 pM ($1.25 \times 10^{-10}$ M) or less, 105 pM ($1.05 \times 10^{-10}$ M) or less, 50 pM ($5.0 \times 10^{-11}$M) or less, or 20 pM ($2.0 \times 10^{-11}$M) or less, as determined by a Kinetic Exclusion Assay, conducted by the method of Rathanaswami et al. (2008) (Rathanaswami et al., High affinity binding measurements of antibodies to cell-surface-expressed antigens, *Analytical Biochemistry* 373: 52-60 (2008; see, e.g., Example 15 herein).

Antigen binding proteins also include peptibodies. The term "peptibody" refers to a molecule comprising an antibody Fc domain attached to at least one peptide. The production of peptibodies is generally described in PCT publication WO 00/24782, published May 4, 2000. Any of these peptides may be linked in tandem (i.e., sequentially), with or without linkers. Peptides containing a cysteinyl residue may be cross-linked with another Cys-containing peptide, either or both of which may be linked to a vehicle. Any peptide having more than one Cys residue may form an intrapeptide disulfide bond, as well. Any of these peptides may be derivatized, for example the carboxyl terminus may be capped with an amino group, cysteines may be cappe, or amino acid residues may substituted by moieties other than amino acid residues (see, e.g., Bhatnagar et al., *J. Med. Chem.* 39: 3814-9 (1996), and Cuthbertson et al., *J. Med. Chem.* 40: 2876-82 (1997), which are incorporated by reference herein in their entirety). The peptide sequences may be optimized, analogous to affinity maturation for antibodies, or otherwise altered by alanine scanning or random or directed mutagenesis followed by screening to identify the best binders. Lowman, *Ann. Rev. Biophys. Biomol. Struct.* 26: 401-24 (1997). Various molecules can be inserted into the antigen binding protein structure, e.g., within the peptide portion itself or between the peptide and vehicle portions of the antigen binding proteins, while retaining the desired activity of antigen binding protein. One can readily insert, for example, molecules such as an Fc domain or fragment thereof, polyethylene glycol or other related molecules such as dextran, a fatty acid, a lipid, a cholesterol group, a small carbohydrate, a peptide, a detectable moiety as described herein (including fluorescent agents, radiolabels such as radioisotopes), an oligosaccharide, oligonucleotide, a polynucleotide, interference (or other) RNA, enzymes, hormones, or the like. Other molecules suitable for insertion in this fashion will be appreciated by those skilled in the art, and are encompassed within the scope of the invention. This includes insertion of, for example, a desired molecule in between two consecutive amino acids, optionally joined by a suitable linker.

The term "recombinant" indicates that the material (e.g., a nucleic acid or a polypeptide) has been artificially or synthetically (i.e., non-naturally) altered by human intervention. The alteration can be performed on the material within, or removed from, its natural environment or state. For example, a "recombinant nucleic acid" is one that is made by recombining nucleic acids, e.g., during cloning, DNA shuffling or other well known molecular biological procedures. Examples of such molecular biological procedures are found in Maniatis et al., *Molecular Cloning. A Laboratory Manual.* Cold Spring Harbor Laboratory, Cold Spring Harbor, N.Y. (1982). A "recombinant DNA molecule," is comprised of segments of DNA joined together by means of such molecular biological techniques. The term "recombinant protein" or "recombinant polypeptide" as used herein refers to a protein molecule which is expressed using a recombinant DNA molecule. A "recombinant host cell" is a cell that contains and/or expresses a recombinant nucleic acid.

The term "polynucleotide" or "nucleic acid" includes both single-stranded and double-stranded nucleotide polymers containing two or more nucleotide residues. The nucleotide residues comprising the polynucleotide can be ribonucleotides or deoxyribonucleotides or a modified form of either type of nucleotide. Said modifications include base modifications such as bromouridine and inosine derivatives, ribose modifications such as 2',3'-dideoxyribose, and internucleotide linkage modifications such as phosphorothioate, phosphorodithioate, phosphoroselenoate, phosphorodiselenoate, phosphoroanilothioate, phosphoraniladate and phosphoroamidate.

The term "oligonucleotide" means a polynucleotide comprising 200 or fewer nucleotide residues. In some embodiments, oligonucleotides are 10 to 60 bases in length. In other embodiments, oligonucleotides are 12, 13, 14, 15, 16, 17, 18, 19, or 20 to 40 nucleotides in length. Oligonucleotides may be single stranded or double stranded, e.g., for use in the construction of a mutant gene. Oligonucleotides may be sense or antisense oligonucleotides. An oligonucleotide can include a label, including an isotopic label (e.g., $^{125}$I, $^{14}$C, $^{13}$C, $^{35}$S, $^{3}$H, $^{2}$H, $^{13}$N, $^{15}$N, $^{18}$O, etc.), for ease of quantification or detection, a fluorescent label, a hapten or an antigenic label, for detection assays. Oligonucleotides may be used, for example, as PCR primers, cloning primers or hybridization probes.

A "polynucleotide sequence" or "nucleotide sequence" or "nucleic acid sequence," as used interchangeably herein, is the primary sequence of nucleotide residues in a polynucleotide, including of an oligonucleotide, a DNA, and RNA, a nucleic acid, or a character string representing the primary sequence of nucleotide residues, depending on context. From any specified polynucleotide sequence, either the given nucleic acid or the complementary polynucleotide sequence can be determined. Included are DNA or RNA of genomic or synthetic origin which may be single- or double-stranded, and represent the sense or antisense strand. Unless specified otherwise, the left-hand end of any single-stranded polynucleotide sequence discussed herein is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA transcript that are 5' to the 5' end of the RNA transcript are referred to as "upstream sequences;" sequence regions on the DNA strand having the same sequence as the RNA transcript that are 3' to the 3' end of the RNA transcript are referred to as "downstream sequences."

"Orientation" refers to the order of nucleotides in a given DNA sequence. For example, an orientation of a DNA sequence in opposite direction in relation to another DNA sequence is one in which the 5' to 3' order of the sequence in relation to another sequence is reversed when compared to a point of reference in the DNA from which the sequence was obtained. Such reference points can include the direction of transcription of other specified DNA sequences in the source DNA and/or the origin of replication of replicable vectors containing the sequence. The 5' to 3' DNA strand is designated, for a given gene, as "sense," "plus" or "coding" strand. The complementary 3' to 5' strand relative to the "plus" strand is described as "antisense," "minus" or "not coding."

As used herein, an "isolated nucleic acid molecule" or "isolated nucleic acid sequence" is a nucleic acid molecule that is either (1) identified and separated from at least one contaminant nucleic acid molecule with which it is ordinarily associated in the natural source of the nucleic acid or (2) cloned, amplified, tagged, or otherwise distinguished from background nucleic acids such that the sequence of the nucleic acid of interest can be determined. An isolated nucleic acid molecule is other than in the form or setting in which it is found in nature. However, an isolated nucleic acid molecule includes a nucleic acid molecule contained in cells that ordinarily express a polypeptide (e.g., an oligopeptide or antibody) where, for example, the nucleic acid molecule is in a chromosomal location different from that of natural cells.

As used herein, the terms "nucleic acid molecule encoding," "DNA sequence encoding," and "DNA encoding" refer to the order or sequence of deoxyribonucleotides along a strand of deoxyribonucleic acid. The order of these deoxyribonucleotides determines the order of ribonucleotides along the mRNA chain, and also determines the order of amino acids along the polypeptide (protein) chain. The DNA sequence thus codes for the RNA sequence and for the amino acid sequence.

The term "gene" is used broadly to refer to any nucleic acid associated with a biological function. Genes typically include coding sequences and/or the regulatory sequences required for expression of such coding sequences. The term "gene" applies to a specific genomic or recombinant sequence, as well as to a cDNA or mRNA encoded by that sequence. A "fusion gene" contains a coding region that encodes a polypeptide with portions from different proteins that are not naturally found together, or not found naturally together in the same sequence as present in the encoded fusion protein (i.e., a chimeric protein). Genes also include non-expressed nucleic acid segments that, for example, form recognition sequences for other proteins. Non-expressed regulatory sequences including transcriptional control elements to which regulatory proteins, such as transcription factors, bind, resulting in transcription of adjacent or nearby sequences.

"Expression of a gene" or "expression of a nucleic acid" means transcription of DNA into RNA (optionally including modification of the RNA, e.g., splicing), translation of RNA into a polypeptide (possibly including subsequent post-translational modification of the polypeptide), or both transcription and translation, as indicated by the context.

As used herein the term "coding region" or "coding sequence" when used in reference to a structural gene refers to the nucleotide sequences which encode the amino acids found in the nascent polypeptide as a result of translation of an mRNA molecule. The coding region is bounded, in eukaryotes, on the 5' side by the nucleotide triplet "ATG" which encodes the initiator methionine and on the 3' side by one of the three triplets which specify stop codons (i.e., TAA, TAG, TGA).

The term "control sequence" or "control signal" refers to a polynucleotide sequence that can, in a particular host cell, affect the expression and processing of coding sequences to which it is ligated. The nature of such control sequences may depend upon the host organism. In particular embodiments, control sequences for prokaryotes may include a promoter, a ribosomal binding site, and a transcription termination sequence. Control sequences for eukaryotes may include promoters comprising one or a plurality of recognition sites for transcription factors, transcription enhancer sequences or elements, polyadenylation sites, and transcription termination sequences. Control sequences can include leader sequences and/or fusion partner sequences. Promoters and enhancers consist of short arrays of DNA that interact specifically with cellular proteins involved in transcription (Maniatis, et al., *Science* 236:1237 (1987)). Promoter and regulatory elements have been isolated from a variety of eukaryotic sources including genes in yeast, insect and mammalian cells and viruses (analogous control elements, i.e., promoters, are also found in prokaryotes). The selection of a particular promoter and enhancer depends on what cell type is to be used to express the protein of interest. Some eukaryotic promoters and enhancers have a broad host range while others are functional in a limited subset of cell types (See, Voss, et al., *Trends Biochem. Sci.*, 11:287 (1986) and Maniatis, et al., *Science* 236:1237 (1987); Magnusson et al., Sustained, high transgene expression in liver with plasmid vectors using optimized promoter-enhancer combinations, *Journal of Gene Medicine* 13(7-8):382-391 (2011); Xu et al., Optimization of transcriptional regulatory elements for constructing plasmid vectors, *Gene.* 272(1-2):149-156 (2001)). Enhancers are generally cis-acting, and in nature, are located up to 1 million base pairs away from the expressed gene on a chromosome. In some cases, an enhancer's orientation may be reversed without affecting its function.

The term "regulatory element" refers to a polynucleotide sequence which functions to shield a promoter or enhancer from silencing effects of the chromatin environment, such as DNA methylation, histone deacetylation or other modifications to the chromatin structures which would otherwise prevent the transcription of the promoter. Such promoter silencing is the result of epigenetic control and can result in a loss of expression over time (See Li. et al., The role of chromatin during transcription. *Cell.* 128:707-719 (2007); Pikaart M J. Loss of transcriptional activity of a transgene is accompanied by DNA methylation and histone deacetylation and is prevented by insulators. Genes Dev. 12:2852-62. (1998)). "Regulatory element" could also refer to DNA sequences which act as barriers to prevent distal enhancer sequences from activating a promoter. Examples of DNA regulatory elements that have chromatin shielding or insulating activity include insulator elements, STAR elements, UCOE elements or MAR elements (see Otte A P et. al. Various expression-augmenting DNA elements benefit from STAR-Select, a nove high stringency selection system for protein expression. Biotechnol Prog. 23(4):801-7 (2007); Ferrari S et al. Chromatin domains boundaries delimited by a histone binding protein in yeast. J. Biol Chem. 279:55520-30 (2001); Kellum R. et al. A group of scs elements function as domain boundaries in an enhancer-blocking assay. Mol. Cell Biol. 12: 2424-31 (1992); Chung J H et al. A 5' element of the chicken beta-globin domain serves as an insulator in human erythroid cells and protects against position effect in *Drosophila*. Cell. 74:505-14 (1993); Williams S et al. CpG Island fragments from HNRAP2B1/CBX3 genomic locus reduce silencing and enhance transgene expression from the hCMV promoter/enhance in mammalian cells. BMC Biotechnol. 5:17 (2005)). Such elements have been isolated from a variety of eukaryotic sources and shown to enhance activity when paired with particular promoter and enhancer. Activity of the regulatory elements depends on what cell type is to be used to express the protein of interest, and the sequence of the element and specific promoter. The regulatory element(s) can be placed in any orientation, but typically must be empirically tested for optimal activity.

The term "vector" means any molecule or entity (e.g., nucleic acid, plasmid, bacteriophage or virus) used to transfer protein coding information into a host cell.

The term "expression vector" or "expression construct" as used herein refers to a recombinant DNA molecule containing a desired coding sequence and appropriate nucleic acid control sequences necessary for the expression of the operably linked coding sequence in a particular host cell. An expression vector can include, but is not limited to, sequences that affect or control transcription, translation, and, if introns are present, affect RNA splicing of a coding region operably linked thereto. Nucleic acid sequences necessary for expression in prokaryotes include a promoter, optionally an operator sequence, a ribosome binding site and possibly other sequences. Eukaryotic cells are known to utilize promoters, enhancers, and termination and polyadenylation signals. A secretory signal peptide sequence can also, optionally, be encoded by the expression vector, operably linked to the coding sequence of interest, so that the expressed polypeptide can be secreted by the recombinant host cell, for more facile isolation of the polypeptide of interest from the cell, if desired. Such techniques are well known in the art. (E.g., Goodey, Andrew R.; et al., Peptide and DNA sequences, U.S. Pat. No. 5,302,697; Weiner et al., Compositions and methods for protein secretion, U.S. Pat. No. 6,022,952 and U.S. Pat. No. 6,335,178; Uemura et al., Protein expression vector and utilization thereof, U.S. Pat. No. 7,029,909; Ruben et al., 27 human secreted proteins, US 2003/0104400 A1).

An expression vector contains one or more expression cassettes. An "expression cassette," at a minimum, contains a promoter, an exogenous gene of interest ("GOI") to be expressed, and a polyadenylation site and/or other suitable terminator sequence. The promoter typically includes a suitable TATA box or G-C-rich region 5' to, but not necessarily directly adjacent to, the transcription start site.

The terms "in operable combination", "in operable order" and "operably linked" as used interchangeably herein refer to the linkage of two or more nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced. For example, a control sequence in a vector that is "operably linked" to a protein coding sequence is ligated thereto so that expression of the protein coding sequence is achieved under conditions compatible with the transcriptional activity of the control sequences. For example, a promoter and/or enhancer sequence, including any combination of cis-acting transcriptional control elements is operably linked to a coding sequence if it stimulates or modulates the transcription of the coding sequence in an appropriate host cell or other expression system. Promoter regulatory sequences that are operably linked to the transcribed gene sequence are physically contiguous to the transcribed sequence, but cis-acting regulatory element sequences that are operably linked to the promoter and/or to a transcribed gene sequence can be operably linked thereto even if the regulatory element is non-contiguous to the promoter sequence and/or transcribed gene sequence. In some useful embodiments of the invention the regulatory element can be situated 5' to the GAPDH promoter-driven expression cassette, and in other useful embodiments the enhancer can be positioned 3' to the GAPDH promoter-driven expression cassette.

As used herein with respect to one candidate nucleic acid sequence having a certain amount or percentage of "sequence identity" or being a certain amount or percentage "identical" to a reference nucleic acid sequence, these terms refer to the percentage of nucleotides in the candidate nucleic acid sequence that are identical with the reference nucleic acid sequence (e.g., percentage of sequential nucleotides identical to SEQ ID NO:35 or SEQ ID NO: 38), after aligning the sequences and introducing gaps, if necessary, to achieve the maximum percent sequence identity. Thus, sequence identity can be determined by standard methods that are commonly used to compare the similarity in position of the nucleotides of two nucleic acid sequences (e.g., BLASTN program). Usually the nucleic acid sequence identity of the candidate sequence to the reference sequence is at least 80%, preferably at least 85%, more preferably at least 90%, and most preferably at least 95%, in particular 96%, more particular 97%, even more particular 98%, most particular 99%, including for example, 80%, 81%, 82%, 83%, 84%, 85%, 86%, 87%, 88%, 89%, 90%, 91%, 92%, 93%, 94%, 95%, 96%, 97%, 98%, 99%, and 100%.

The term "host cell" means a cell that has been transformed, or is capable of being transformed, with a nucleic acid and thereby expresses a gene of interest. The term includes the progeny of the parent cell, whether or not the progeny is identical in morphology or in genetic make-up to the original parent cell, so long as the gene of interest is present. Any of a large number of available and well-known host cells may be used in the practice of this invention, but a CHO cell line is preferred. The selection of a particular host is dependent upon a number of factors recognized by the art. These include, for example, compatibility with the chosen expression vector, toxicity of the peptides encoded by the DNA molecule, rate of transformation, ease of recovery of the peptides, expression characteristics, biosafety and costs. A balance of these factors must be struck with the understanding that not all hosts may be equally effective for the expression of a particular DNA sequence. Within these general guidelines, useful microbial host cells in culture include bacteria (such as *Escherichia coli* sp.), yeast (such as *Saccharomyces* sp.) and other fungal cells, insect cells, plant cells, mammalian (including human) host cells, e.g., CHO cells and HEK-293 cells. Modifications can be made at the DNA level, as well. The peptide-encoding DNA sequence may be changed to codons more compatible with the chosen host cell. For *E. coli*, optimized codons are known in the art. Codons can be substituted to eliminate restriction sites or to include silent restriction sites, which may aid in processing of the DNA in the selected host cell. Next, the transformed host is cultured and purified. Host cells may be cultured under conventional fermentation conditions so that the desired compounds are expressed. Such fermentation conditions are well known in the art.

The term "transfection" means the uptake of foreign or exogenous DNA by a cell, and a cell has been "transfected" when the exogenous DNA has been introduced inside the cell membrane. A number of transfection techniques are well known in the art and are disclosed herein. See, e.g., Graham et al., 1973, Virology 52:456; Sambrook et al., 2001, *Molecular Cloning: A Laboratory Manual*, supra; Davis et al., 1986, Basic Methods in Molecular Biology, Elsevier; Chu et al., 1981, Gene 13:197. Such techniques can be used to introduce one or more exogenous DNA moieties into suitable host cells.

The term "transformation" refers to a change in a cell's genetic characteristics, and a cell has been transformed when it has been modified to contain new DNA or RNA. For example, a cell is transformed where it is genetically modified from its native state by introducing new genetic material via transfection, transduction, or other techniques. Following transfection or transduction, the transforming DNA may recombine with that of the cell by physically integrating into a chromosome of the cell, or may be maintained transiently as an episomal element without being replicated, or may replicate independently as a plasmid. A cell is considered to have been "stably transformed" when the transforming DNA is replicated with the division of the cell.

A "domain" or "region" (used interchangeably herein) of a protein is any portion of the entire protein, up to and including the complete protein, but typically comprising less than the complete protein. A domain can, but need not, fold independently of the rest of the protein chain and/or be correlated with a particular biological, biochemical, or structural function or location (e.g., a ligand binding domain, or a cytosolic, transmembrane or extracellular domain).

A "therapeutic candidate" is any compound, tool compound, combination of compounds, small molecule, polypeptide, peptide, antigen binding protein, antibody or other proteinaceous molecule or biologic, that has or potentially may have therapeutic value in treating, preventing, or mitigating a disease or disorder. The therapeutic candidate is pharmacologically active. The term "pharmacologically active" means that a substance so described is determined to have activity that affects a medical parameter (e.g., blood pressure, blood cell count, cholesterol level, pain perception) or disease state (e.g., cancer, autoimmune disorders, chronic pain). Conversely, the term "pharmacologically inactive" means that no activity affecting a medical parameter or disease state can be determined for that substance. Thus, pharmacologically active molecules, comprise agonistic or mimetic and antagonistic molecules as defined below.

The terms "-mimetic peptide," "peptide mimetic," and "-agonist peptide" refer to a peptide or protein having biological activity comparable to a naturally occurring protein of interest. These terms further include peptides that indirectly mimic the activity of a naturally occurring peptide molecule, such as by potentiating the effects of the naturally occurring molecule.

An "agonist" is a molecule that binds to a receptor of interest and triggers a response by the cell bearing the receptor. Agonists often mimic the action of a naturally occurring substance. An "inverse agonist" causes an action opposite to that of the agonist.

The term "antagonist" and "inhibitor" refer to a molecule that blocks or in some way interferes with the biological activity of a receptor of interest, or has biological activity comparable to a known antagonist or inhibitor of a receptor of interest (such as, but not limited to, an ion channel or a G-Protein Coupled Receptor (GPCR)).

A "tool compound" is any small molecule, peptide, antigen binding protein, antibody or other proteinaceous molecule, employed as a reagent used in an experiment, as a control, or as a pharmacologically active surrogate compound in place of a therapeutic candidate.

The term "exogenous" refers to an isolated nucleotide sequence, originating in a different species from the host cell, that may be inserted into the mammalian host cell. The exogenous gene of interest optionally may be operably linked to other genetic elements (such as a promoter, poly A sequence and the like) that may serve to modulate, either directly, or indirectly in conjunction with the cellular machinery, the transcription and/or expression of the gene. Alternatively or additionally, the exogenous gene may be linked to nucleotide sequences that aid in integration of the gene into the chromosomal DNA of the mammalian cell nucleus (as for example, in homologous recombination). The exogenous gene may be comprised of a nucleotide sequence that is either homologous or heterologous to a particular nucleotide sequence in the mammal's genome, or is a hybrid sequence (i.e. one or more portions of the gene are homologous, and one or more portions are heterologous to the mammal's genetic material). The gene nucleotide sequence of interest may encode a polypeptide or a variant of a polypeptide, found endogenously in the mammal, it may encode a polypeptide not naturally occurring in the mammal (i.e. an exogenous polypeptide), or it may encode a hybrid of endogenous and exogenous polypeptides. Where the gene of interest is operably linked to a promoter, the promoter may be homologous or heterologous to the mammal and/or to the gene of interest. Alternatively, the promoter may be a hybrid of endogenous and exogenous promoter elements (enhancers, silencers, suppressors, and the like).

Selection of Gene(s).

Typically, the exogenous gene(s) useful in the present invention will be a nucleotide sequence encoding a polypeptide of interest (not hamster GAPDH), e.g., a target binding polypeptide, such as an antibody or antibody fragment, a protein or peptide ligand of a receptor, a polypeptide involved in the nervous system, an immune response, hematopoiesis, inflammation, cell growth and proliferation, cell lineage differentiation, and/or the stress response. Included within the scope of this invention is the insertion of one, two, or more exogenous genes of interest into the host cell.

Where more than one gene of interest is used in this invention, the genes may be prepared and inserted individually, or may be generated together as one construct for insertion. The genes may be homologous or heterologous to both the promoter selected to drive expression of each gene and/or to the mammal. Further, the gene may be a full length cDNA or genomic DNA sequence, or any fragment, subunit or mutant thereof that has at least some biological activity i.e., exhibits an effect at any level (biochemical, cellular and/or morphological) that is not readily observed in a wild type, non-transgenic mammal of the same species. Optionally, the gene of interest can be a hybrid nucleotide sequence, i.e., one constructed from homologous and/or heterologous cDNA and/or genomic DNA fragments. The gene may also optionally be a mutant of one or more naturally occurring cDNA and/or genomic sequences, or an allelic variant thereof.

Each gene may be isolated and obtained in suitable quantity using one or more methods that are well known in the art. These methods and others useful for isolating a gene are set forth, for example, in Sambrook et al. (Molecular Cloning: A Laboratory Manual, Cold Spring Harbor Laboratory Press, Cold Spring Harbor, N.Y. [1989]) and in Berger and Kimmel (*Methods in Enzymology: Guide to Molecular Cloning Techniques*, vol. 152, Academic Press, Inc., San Diego, Calif [1987]).

Where the nucleotide sequence of each gene is known, the gene may be synthesized, in whole or in part, using chemical synthesis methods such as those described in Engels et al. (*Angew. Chem. Int. Ed. Engl.*, 28:716-734 [1989]). These methods include, inter alia, the phosphotriester, phosphoramidite and H-phosphonate methods of nucleic acid synthesis. Alternatively, the gene may be obtained by screening an appropriate cDNA or genomic library using one or more nucleic acid probes (oligonucleotides, cDNA or genomic DNA fragments with an acceptable level of homology to the gene to be cloned, and the like) that will hybridize selectively with the DNA sequence of the gene of interest. Another suitable method for obtaining a gene sequence is the polymerase chain reaction (PCR). However, successful use of this method requires that enough information about the nucleotide sequence of the gene of interest be available so as to design suitable oligonucleotide primers useful for amplification of the appropriate nucleotide sequence.

Where the method of choice requires the use of oligonucleotide primers or probes (e.g. PCR, cDNA or genomic library screening), the oligonucleotide sequences selected as probes or primers should be of adequate length and sufficiently unambiguous so as to minimize the amount of non-specific binding that will occur during library screening or PCR. The actual sequence of the probes or primers is usually based on conserved or highly homologous sequences or regions from the same or a similar gene from another organism. Optionally, the probes or primers can be degenerate.

In cases where only the expressed amino acid sequence of the gene of interest is known, a probable and functional nucleic acid sequence may be inferred for the gene using known and preferred codons for each amino acid residue. This sequence can then be chemically synthesized.

This invention encompasses the use of gene mutant sequences. A mutant gene is a gene containing one or more nucleotide substitutions, deletions, and/or insertions as compared to the wild type sequence. The nucleotide substitution, deletion, and/or insertion can give rise to a gene product (i.e., protein) that is different in its amino acid sequence from the wild type amino acid sequence. Preparation of such mutants is well known in the art, and is described for example in Wells et al. (*Gene*, 34:315 [1985]), and in Sambrook et al, supra.

Selection of Control Sequences and Regulatory Elements.

Genes are typically operably linked to promoters, where a promoter is selected to regulate expression of each gene in a particular manner. Within the scope of the present invention, a hamster glyceraldehyde-3-phosphate dehydrogenase (GAPDH) promoter is preferred for expression in CHO cells. For example, the hamster GAPDH promoter sequence from Gene ID: 100736557 (NCBI Reference Sequence NW_003613610.1) can be cloned and used in the inventive expression vector.

In some useful examples of the inventive expression vector, the hamster GAPDH promoter comprises the nucleotide sequence of SEQ ID NO:50 (nucleotide positions −532 through −23 in relation to the GAPDH transcription start site), or an operable fragment thereof. The hamster GAPDH promoter sequence (SEQ ID NO:50) was cloned from Chinese hamster (*Cricetulus griseus*) genomic DNA. Larger fragments of the hamster GAPDH gene sequence that include the GAPDH promoter sequence (SEQ ID NO:50), for example SEQ ID NO:49 (nucleotide positions −532 through +305 in relation to the GAPDH transcription start site), which contains the first exon and intron of hamster GAPDH, can also be used to provide the hamster GAPDH promoter. Larger fragments of the hamster GAPDH gene that include the promoter sequence can also be used in the expression vector, such as SEQ ID NO:11 (−2049 through +2161 relative to transcription start site), which includes, inter alia, introns 1 and 2 of the hamster GAPDH gene. It is more efficient to use a fragment that does not include intron 1 (SEQ ID NO:51; nucleotide positions +64 through +293 relative to the transcription start site of the Chinese hamster GAPDH gene). However, the effectiveness of the inventive expression vector is improved by the inclusion therein, 3' to the GAPDH promoter and 5' to the gene of interest, of the nucleotide sequence of SEQ ID NO:52 (i.e., intron 2).

Where more than one exogenous gene of interest is to be used, each gene may be regulated by the same or by a different promoter. Besides the hamster GAPDH promoter, the selected promoters may be homologous (i.e., from the same species as the mammal to be transfected with the gene of interest) or heterologous (i.e., from a source other than the species of the mammal to be transfected with the gene). As such, the source of each promoter may be from any unicellular, prokaryotic or eukaryotic organism, or any vertebrate or invertebrate organism.

Selection of Other Vector Components

In addition to the gene of interest and the promoter, the vectors useful for preparing the gene(s) of interest for the practice of this invention typically contain one or more other elements useful for (1) optimal expression of gene in the mammal into which the gene is inserted, and (2) amplification of the vector in bacterial or mammalian host cells. Each of these elements will be positioned appropriately in the vector with respect to each other element so as to maximize their respective activities. Such positioning is well known to the ordinary skilled artisan. The following elements may be optionally included in the vector as appropriate.

i. Signal Sequence Element

For those embodiments of the invention where the polypeptide encoded by the gene of interest is to be secreted, a small polypeptide termed signal sequence is frequently present to direct the polypeptide encoded by the gene out of the cell where it is synthesized. Typically, the signal sequence is positioned in the coding region of the gene towards or at the 5' end of the coding region. Many signal sequences have been identified, and those that are functional and thus compatible with expression by cells from various tissue types may be used in conjunction with the gene of interest. Therefore, the nucleotide sequence encoding the signal sequence may be homologous or heterologous to the gene, and may be homologous or heterologous to the mammalian species from which the cell was derived. Additionally, the nucleotide sequence encoding the signal sequence may be chemically synthesized using methods set forth above. However, for purposes herein, preferred signal sequences are those that occur naturally with the gene of interest (i.e., are homologous to the gene).

ii. Membrane Anchoring Domain Element

In some cases, it may be desirable to have a gene of interest expressed on the surface of a particular intracellular membrane or on the plasma membrane. Naturally occurring membrane proteins contain, as part of the polypeptide, a stretch of amino acids that serve to anchor the protein to the membrane. However, for proteins that are not naturally found on the membrane, such a stretch of amino acids may be added to confer this feature. Frequently, the anchor domain will be an internal portion of the polypeptide sequence and thus the nucleotide sequence encoding it will be engineered into an internal region of the gene's nucleotide sequence. However, in other cases, the nucleotide sequence encoding the anchor domain may be attached to the 5' or 3' end of the gene's nucleotide sequence. Here, the nucleotide sequence encoding the anchor domain may first be placed into the vector in the appropriate position as a separate component from the nucleotide sequence encoding the gene of interest. As for the signal sequence, the anchor domain may be from any source and thus may be homologous or heterologous with respect to both the gene and the mammalian species from which the host cell was derived. Alternatively, the anchor domain may be chemically synthesized using methods set forth above.

iii. Origin of Replication Element

This component is typically a part of prokaryotic expression vectors purchased commercially, and aids in the amplification of the vector in a host cell. If the vector of choice does not contain an origin of replication site, one may be chemically synthesized based on a known sequence, and ligated into the vector.

iv. Transcription Termination Element

This element, also known as the polyadenylation or polyA sequence, is typically located 3' to the gene's nucleotide sequence in the vector, and serves to terminate transcription of the gene of interest. While the nucleotide sequence encoding this element is easily cloned from a library or even purchased commercially as part of a vector, it can also be readily synthesized using methods for nucleotide sequence synthesis such as those described above.

v. Intron Element In many cases, transcription of the gene of interest is increased by the presence of one intron or more than one intron (linked by exons) on the cloning vector. The intron(s) may be naturally occurring within the gene nucleotide sequence, especially where the gene is a full length or a fragment of a genomic DNA sequence. Where the intron(s) is not naturally occurring within the nucleotide sequence (as for most cDNAs), the intron(s) may be obtained from another source. The intron(s) may be homologous or heterologous to the gene of interest and/or to the mammalian species from which the host cell was derived. The position of the intron with respect to the promoter and the gene of interest is important, as the intron must be transcribed to be effective. As such, where the gene is a cDNA sequence, the preferred position for the intron(s) is 3' to the transcription start site, and 5' to the polyA transcription termination sequence. Preferably for cDNAs, the intron will be located on one side or the other (i.e., 5' or 3') of the gene's nucleotide sequence such that it does not interrupt the gene's nucleotide sequence. Any intron from any source, including any viral, prokaryotic and eukaryotic (plant or animal) organisms, may be used to practice this invention, provided that it is compatible with the host cell(s) into which it is inserted. Also included herein are synthetic introns. Optionally, more than one intron may be used in the vector. A useful set of introns and exons is the human growth hormone (hGH) DNA sequence.

vi. Selectable Marker(s) Element

Selectable marker genes encode polypeptides necessary for the survival and growth of transfected cells grown in a selective culture medium. Typical selection marker genes encode proteins that (a) confer resistance to antibiotics or other toxins, e.g., ampicillin, tetracycline, or kanomycin for prokaryotic host cells, and neomycin, hygromycin, or methotrexate for mammalian cells; (b) complement auxotrophic deficiencies of the cell; or (c) supply critical nutrients not available from complex media, e.g., the gene encoding D-alanine racemase for cultures of Bacilli.

All of the elements set forth above, as well as others useful in this invention, are well known to the skilled artisan and are described, for example, in Sambrook et al. (*Molecular Cloning: A Laboratory Manual*, Cold Spring Harbor Laboratory Press, Cold Spring Harbor, N.Y. [1989]) and Berger et al., eds. (*Guide to Molecular Cloning Techniques*, Academic Press, Inc., San Diego, Calif [1987]).

Construction of Cloning Vectors

The cloning vectors most useful for amplification of gene cassettes useful in preparing the recombinant expression vectors of this invention are those that are compatible with prokaryotic cell hosts. However, eukaryotic cell hosts, and vectors compatible with these cells, are within the scope of the invention.

In certain cases, some of the various elements to be contained on the cloning vector may be already present in commercially available cloning or amplification vectors such as pUC18, pUC19, pBR322, the pGEM vectors (Promega Corp, Madison, Wis.), the pBluescript® vectors such as pBIISK+/−(Stratagene Corp., La Jolla, Calif.), and the like, all of which are suitable for prokaryotic cell hosts. In this case it is necessary to only insert the gene(s) of interest into the vector.

However, where one or more of the elements to be used are not already present on the cloning or amplification vector, they may be individually obtained and ligated into the vector. Methods used for obtaining each of the elements and ligating them are well known to the skilled artisan and are comparable to the methods set forth above for obtaining a gene of interest (i.e., synthesis of the DNA, library screening, and the like).

Vectors used for cloning or amplification of the nucleotide sequences of the gene(s) of interest and/or for transfection of the mammalian host cells are constructed using methods well known in the art. Such methods include, for example, the standard techniques of restriction endonuclease digestion, ligation, agarose and acrylamide gel purification of DNA and/or RNA, column chromatography purification of DNA and/or RNA, phenol/chloroform extraction of DNA, DNA sequencing, polymerase chain reaction amplification, and the like, as set forth in Sambrook et al., supra.

The final vector used to practice this invention is typically constructed from a starting cloning or amplification vector such as a commercially available vector. This vector may or may not contain some of the elements to be included in the completed vector. If none of the desired elements are present in the starting vector, each element may be individually ligated into the vector by cutting the vector with the appropriate restriction endonuclease(s) such that the ends of the element to be ligated in and the ends of the vector are compatible for ligation. In some cases, it may be necessary to "blunt" the ends to be ligated together in order to obtain a satisfactory ligation. Blunting is accomplished by first filling in "sticky ends" using Klenow DNA polymerase or T4 DNA polymerase in the presence of all four nucleotides. This procedure is well known in the art and is described for example in Sambrook et al., supra.

Alternatively, two or more of the elements to be inserted into the vector may first be ligated together (if they are to be positioned adjacent to each other) and then ligated into the vector.

One other method for constructing the vector is to conduct all ligations of the various elements simultaneously in one reaction mixture. Here, many nonsense or nonfunctional vectors will be generated due to improper ligation or insertion of the elements, however the functional vector may be identified and selected by restriction endonuclease digestion.

After the vector has been constructed, it may be transfected into a prokaryotic host cell for amplification. Cells typically used for amplification are *E coli* DH5-alpha (Gibco/BRL, Grand Island, N.Y.) and other *E. coli* strains with characteristics similar to DH5-alpha.

Where mammalian host cells are used, cell lines such as Chinese hamster ovary (CHO cells; Urlab et al., *Proc. Natl. Acad. Sci USA,* 77:4216 [1980])) and human embryonic kidney cell line 293 (Graham et al., *J. Gen. Virol.,* 36:59 [1977]), as well as other lines, are suitable.

Transfection of the vector into the selected host cell line for amplification is accomplished using such methods as calcium phosphate, electroporation, microinjection, lipofection or DEAE-dextran. The method selected will in part be a function of the type of host cell to be transfected. These methods and other suitable methods are well known to the skilled artisan, and are set forth in Sambrook et al., supra.

After culturing the cells long enough for the vector to be sufficiently amplified (usually overnight for *E. coli* cells), the vector (often termed plasmid at this stage) is isolated from the cells and purified. Typically, the cells are lysed and the plasmid is extracted from other cell contents. Methods suitable for plasmid purification include inter alia, the alkaline lysis mini-prep method (Sambrook et al., supra).

Preparation of Plasmid for Insertion

Typically, the plasmid containing the gene of interest is linearized, and portions of it removed using a selected restriction endonuclease prior to insertion into the embryo. In some cases, it may be preferable to isolate the gene, promoter, other control sequences, and regulatory elements as a linear fragment from the other portions of the vector, thereby injecting only a linear nucleotide sequence containing the gene, promoter, intron (if one is to be used), enhancer, polyA sequence, and optionally a signal sequence or membrane anchoring domain into the embryo. This may be accomplished by cutting the plasmid so as to remove the nucleic acid sequence region containing these elements, and purifying this region using agarose gel electrophoresis or other suitable purification methods.

Therapeutic Candidate Compounds

Production of Antibodies

Polyclonal Antibodies.

Polyclonal antibodies are typically raised in animals by multiple subcutaneous (sc) or intraperitoneal (ip) injections of the relevant antigen and an adjuvant. Alternatively, antigen may be injected directly into the animal's lymph node (see Kilpatrick et al., *Hybridoma*, 16:381-389, 1997). An improved antibody response may be obtained by conjugating the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride or other agents known in the art.

Animals are immunized against the antigen, immunogenic conjugates, or derivatives by combining, e.g., 100 µg of the protein or conjugate (for mice) with 3 volumes of Freund's complete adjuvant and injecting the solution intradermally at multiple sites. One month later, the animals are boosted with ⅕ to ⅒ the original amount of peptide or conjugate in Freund's complete adjuvant by subcutaneous injection at multiple sites. At 7-14 days post-booster injection, the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies.

Monoclonal antibodies can be produced using any technique known in the art, e.g., by immortalizing spleen cells harvested from the transgenic animal after completion of the immunization schedule. The spleen cells can be immortalized using any technique known in the art, e.g., by fusing them with myeloma cells to produce hybridomas. For example, monoclonal antibodies can be made using the hybridoma method first described by Kohler et al., *Nature*, 256:495 (1975), or can be made by recombinant DNA methods (e.g., Cabilly et al., Methods of producing immunoglobulins, vectors and transformed host cells for use therein, U.S. Pat. No. 6,331,415), including methods, such as the "split DHFR" method, that facilitate the generally equimolar production of light and heavy chains, optionally using mammalian cell lines (e.g., CHO cells) that can glycosylate the antibody (See, e.g., Page, Antibody production, EP0481790 A2 and U.S. Pat. No. 5,545,403).

In the hybridoma method, a mouse or other appropriate host mammal, such as rats, hamster or macaque monkey, is immunized as herein described to elicit lymphocytes that produce or are capable of producing antibodies that will specifically bind to the protein used for immunization. Alternatively, lymphocytes can be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells, once prepared, are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium. Human myeloma and mouse-human heteromyeloma cell lines also have been described for the production of human monoclonal antibodies (Kozbor, *J. Immunol.*, 133: 3001 (1984); Brodeur et al., *Monoclonal Antibody Production Techniques and Applications*, pp. 51-63 (Marcel Dekker, Inc., New York, 1987)). Myeloma cells for use in hybridoma-producing fusion procedures preferably are non-antibody-producing, have high fusion efficiency, and enzyme deficiencies that render them incapable of growing in certain selective media which support the growth of only the desired fused cells (hybridomas). Examples of suitable cell lines for use in mouse fusions include Sp-20, P3-X63/Ag8, P3-X63-Ag8.653, NS1/1.Ag 4 1, Sp210-Ag14, FO, NSO/U, MPC-11, MPC11-X45-GTG 1.7 and S194/5XXO Bul; examples of cell lines used in rat fusions include R210.RCY3, Y3-Ag 1.2.3, IR983F and 4B210. Other cell lines useful for cell fusions are U-266, GM1500-GRG2, LICR-LON-HMy2 and UC729-6.

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA). The binding affinity of the monoclonal antibody can, for example, be determined by BIAcore® or Scatchard analysis (Munson et al., *Anal. Biochem.*, 107:220 (1980); Fischer et al., A peptide-immunoglobulin-conjugate, WO 2007/045463 A1, Example 10, which is incorporated herein by reference in its entirety).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells may be grown in vivo as ascites tumors in an animal.

Hybridomas or mAbs may be further screened to identify mAbs with particular properties, such as binding affinity with a particular antigen or target. The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, affinity chromatography, or any other suitable purification technique known in the art.

Recombinant Production of Antibodies and Other Polypeptides.

Relevant amino acid sequences from an immunoglobulin or polypeptide of interest may be determined by direct protein sequencing, and suitable encoding nucleotide sequences can be designed according to a universal codon table. Alternatively, genomic or cDNA encoding the monoclonal antibodies may be isolated and sequenced from cells producing such antibodies using conventional procedures (e.g., by using oligonucleotide probes that are capable of binding specifically to genes encoding the heavy and light chains of the monoclonal antibodies). Relevant DNA sequences can be determined by direct nucleic acid sequencing.

Cloning of DNA is carried out using standard techniques (see, e.g., Sambrook et al. (1989) Molecular Cloning: A Laboratory Guide, Vols 1-3, Cold Spring Harbor Press, which is incorporated herein by reference). For example, a cDNA library may be constructed by reverse transcription of polyA+mRNA, preferably membrane-associated mRNA, and the library screened using probes specific for human immunoglobulin polypeptide gene sequences. In one embodiment, however, the polymerase chain reaction (PCR) is used to amplify cDNAs (or portions of full-length cDNAs) encoding an immunoglobulin gene segment of interest (e.g., a light or heavy chain variable segment). The amplified sequences can be readily cloned into any suitable vector, e.g., expression vectors, minigene vectors, or phage display vectors. It will be appreciated that the particular method of cloning used is not critical, so long as it is possible to determine the sequence of some portion of the immunoglobulin polypeptide of interest.

One source for antibody nucleic acids is a hybridoma produced by obtaining a B cell from an animal immunized with the antigen of interest and fusing it to an immortal cell. Alternatively, nucleic acid can be isolated from B cells (or whole spleen) of the immunized animal. Yet another source of nucleic acids encoding antibodies is a library of such nucleic acids generated, for example, through phage display technology. Polynucleotides encoding peptides of interest, e.g., variable region peptides with desired binding characteristics, can be identified by standard techniques such as panning.

The sequence encoding an entire variable region of the immunoglobulin polypeptide may be determined; however, it will sometimes be adequate to sequence only a portion of a variable region, for example, the CDR-encoding portion. Sequencing is carried out using standard techniques (see, e.g., Sambrook et al. (1989) Molecular Cloning: A Laboratory Guide, Vols 1-3, Cold Spring Harbor Press, and Sanger, F. et al. (1977) Proc. Natl. Acad. Sci. USA 74: 5463-5467, which is incorporated herein by reference). By comparing the sequence of the cloned nucleic acid with published sequences of human immunoglobulin genes and cDNAs, one of skill will readily be able to determine, depending on the region sequenced, (i) the germline segment usage of the hybridoma immunoglobulin polypeptide (including the isotype of the heavy chain) and (ii) the sequence of the heavy and light chain variable regions, including sequences resulting from N-region addition and the process of somatic mutation. One source of immunoglobulin gene sequence information is the National Center for Biotechnology Information, National Library of Medicine, National Institutes of Health, Bethesda, Md.

Isolated DNA can be operably linked to control sequences or placed into expression vectors, which are then transfected into host cells that do not otherwise produce immunoglobulin protein, to direct the synthesis of monoclonal antibodies in the recombinant host cells. Recombinant production of antibodies is well known in the art.

Nucleic acid is operably linked when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, operably linked means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

Many vectors are known in the art. Vector components may include one or more of the following: a signal sequence (that may, for example, direct secretion of the antibody; e.g., ATGGACATGAGGGTGCCCGCTCAGCTC-CTGGGGCTCCTGCTGCTGTGGCTG AGAGGT-GCGCGCTGT//SEQ ID NO:53, which encodes the VK-1 signal peptide sequence MDMRVPAQLLGLLLLWLR-GARC//SEQ ID NO:54), an origin of replication, one or more selective marker genes (that may, for example, confer antibiotic or other drug resistance, complement auxotrophic deficiencies, or supply critical nutrients not available in the media), an regulatory element, a promoter, and a transcription termination sequence, all of which are well known in the art.

Cell, cell line, and cell culture are often used interchangeably and all such designations herein include progeny. Transformants and transformed cells include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included.

Exemplary host cells include prokaryote, yeast, or higher eukaryote cells. Prokaryotic host cells include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as *Bacillus* such as *B. subtilis* and *B. licheniformis, Pseudomonas*, and *Streptomyces*. Eukaryotic microbes such as filamentous fungi or yeast are suitable cloning or expression hosts for recombinant polypeptides or antibodies. *Saccharomyces cerevisiae*, or common baker's yeast, is the most commonly used among lower eukaryotic host microorganisms. However, a number of other genera, species, and strains are commonly available and useful herein, such as *Pichia*, e.g. *P. pastoris, Schizosaccharomyces pombe; Kluyveromyces, Yarrowia; Candida; Trichoderma reesia; Neurospora crassa; Schwanniomyces* such as *Schwanniomyces occidentalis*; and filamentous fungi such as, e.g., *Neurospora*, *Penicillium*, *Tolypocladium*, and *Aspergillus* hosts such as *A. nidulans* and *A. niger*.

Host cells for the expression of glycosylated antibodies can be derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* have been identified. A variety of viral strains for transfection of such cells are publicly available, e.g., the L-1 variant of *Autographa californica* NPV and the Bm-5 strain of *Bombyx mori* NPV.

Vertebrate host cells are also suitable hosts, and recombinant production of polypeptides (including antibody) from such cells has become routine procedure. Examples of useful mammalian host cell lines are Chinese hamster ovary (CHO) cells of any strain, including but not limited to CHO-K1 cells (ATCC CCL61), DXB-11, CHO-DG-44, CHO-S, CHO-AM1, CHO-DXB11, and Chinese hamster ovary cells/-DHFR (CHO, Urlaub et al., *Proc. Natl. Acad. Sci. USA* 77: 4216 (1980)); monkey kidney CV1 line transformed by SV40 (COS-7, ATCC CRL 1651); human embryonic kidney line (293 or 293 cells subcloned for growth in suspension culture, [Graham et al., *J. Gen Virol.* 36: 59 (1977)]; baby hamster kidney cells (BHK, ATCC CCL 10); mouse sertoli cells (TM4, Mather, Biol. Reprod. 23: 243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human hepatoma cells (Hep G2, HB 8065); mouse mammary tumor (MMT 060562, ATCC CCL51); TRI cells (Mather et al., Annals N.Y Acad. Sci. 383: 44-68 (1982)); MRC 5 cells or FS4 cells; or mammalian myeloma cells.

Host cells are transformed or transfected with the above-described nucleic acids or vectors for production of polypeptides (including antibodies) and are cultured in conventional nutrient media modified as appropriate for inducing promoters, selecting transformants, or amplifying the genes encoding the desired sequences. In addition, novel vectors and transfected cell lines with multiple copies of transcription units separated by a selective marker are particularly useful for the expression of polypeptides, such as antibodies.

The host cells used to produce the polypeptides useful in the invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58: 44 (1979), Barnes et al., *Anal. Biochem.* 102: 255 (1980), U.S. Pat. No. 4,767,704; 4,657,866; 4,927,762; 4,560,655; or 5,122,469; WO90103430; WO 87/00195; or U.S. Pat. Re. No. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as Gentamycin™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

Upon culturing the host cells, the recombinant polypeptide can be produced intracellularly, in the periplasmic space, or directly secreted into the medium. If the polypeptide, such as an antibody, is produced intracellularly, as a first step, the particulate debris, either host cells or lysed fragments, is removed, for example, by centrifugation or ultrafiltration.

An antibody or antibody fragment) can be purified using, for example, hydroxylapatite chromatography, cation or anion exchange chromatography, or preferably affinity chromatography, using the antigen of interest or protein A or protein G as an affinity ligand. Protein A can be used to purify proteins that include polypeptides are based on human γ1, γ2, or γ4 heavy chains (Lindmark et al., *J. Immunol. Meth.* 62: 1-13 (1983)). Protein G is recommended for all mouse isotypes and for human γ3 (Guss et al., *EMBO J.* 5: 15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the protein comprises a $C_H3$ domain, the Bakerbond ABX™ resin (J. T. Baker, Phillipsburg, N.J.) is useful for purification. Other techniques for protein purification such as ethanol precipitation, Reverse Phase HPLC, chromatofocusing, SDS-PAGE, and ammonium sulfate precipitation are also possible depending on the antibody to be recovered.

Chimeric, Humanized, Human Engineered™, Xenomouse® Monoclonal Antibodies.

Chimeric monoclonal antibodies, in which the variable Ig domains of a rodent monoclonal antibody are fused to human constant Ig domains, can be generated using standard procedures known in the art (See Morrison, S. L., et al. (1984) Chimeric Human Antibody Molecules; Mouse Antigen Binding Domains with Human Constant Region Domains, Proc. Natl. Acad. Sci. USA 81, 6841-6855; and, Boulianne, G. L., et al, Nature 312, 643-646. (1984)). A number of techniques have been described for humanizing or modifying antibody sequence to be more human-like, for example, by (1) grafting the non-human complementarity determining regions (CDRs) onto a human framework and constant region (a process referred to in the art as humanizing through "CDR grafting") or (2) transplanting the entire non-human variable domains, but "cloaking" them with a human-like surface by replacement of surface residues (a process referred to in the art as "veneering") or (3) modifying selected non-human amino acid residues to be more human, based on each residue's likelihood of participating in antigen-binding or antibody structure and its likelihood for immunogenicity. See, e.g., Jones et al., *Nature* 321:522 525 (1986); Morrison et al., *Proc. Natl. Acad. Sci., USA.*, 81:6851 6855 (1984); Morrison and Oi, *Adv. Immunol.*, 44:65 92 (1988); Verhoeyer et al., *Science* 239:1534 1536 (1988); Padlan, *Molec. Immun.* 28:489 498 (1991); Padlan, *Molec. Immunol.* 31(3):169 217 (1994); and Kettleborough, C. A. et al., *Protein Eng.* 4(7):773 83 (1991); Co, M. S., et al. (1994), *J. Immunol.* 152, 2968-2976; Studnicka et al. *Protein Engineering* 7: 805-814 (1994); each of which is incorporated herein by reference in its entirety.

A number of techniques have been described for humanizing or modifying antibody sequence to be more human-like, for example, by (1) grafting the non-human complementarity determining regions (CDRs) onto a human framework and constant region (a process referred to in the art as humanizing through "CDR grafting") or (2) transplanting the entire non-human variable domains, but "cloaking" them with a human-like surface by replacement of surface residues (a process referred to in the art as "veneering") or (3) modifying selected non-human amino acid residues to be more human, based on each residue's likelihood of participating in antigen-binding or antibody structure and its likelihood for immunogenicity. See, e.g., Jones et al., *Nature* 321:522 525 (1986); Morrison et al., *Proc. Natl. Acad. Sci., USA.*, 81:6851 6855 (1984); Morrison and Oi, *Adv. Immunol.*, 44:65 92 (1988); Verhoeyer et al., *Science* 239:1534 1536 (1988); Padlan, *Molec. Immun.* 28:489 498 (1991); Padlan, *Molec. Immunol.* 31(3):169 217 (1994); and Kettleborough, C. A. et al., *Protein Eng.* 4(7): 773 83 (1991); Co, M. S., et al. (1994), *J. Immunol.* 152, 2968-2976); Studnicka et al. *Protein Engineering* 7: 805-814 (1994); each of which is incorporated herein by reference in its entirety.

Antibodies can also be produced using transgenic animals that have no endogenous immunoglobulin production and are engineered to contain human immunoglobulin loci. (See, e.g., Mendez et al., *Nat. Genet.* 15:146-156 (1997)) For example, WO 98/24893 discloses transgenic animals having a human Ig locus wherein the animals do not produce functional endogenous immunoglobulins due to the inactivation of endogenous heavy and light chain loci. WO 91/10741 also discloses transgenic non-primate mammalian hosts capable of mounting an immune response to an immunogen, wherein the antibodies have primate constant and/or variable regions, and wherein the endogenous immunoglobulin encoding loci are substituted or inactivated. WO 96/30498 discloses the use of the Cre/Lox system to modify the immunoglobulin locus in a mammal, such as to replace all or a portion of the constant or variable region to form a modified antibody molecule. WO 94/02602 discloses non-human mammalian hosts having inactivated endogenous Ig loci and functional human Ig loci. U.S. Pat. No. 5,939,598 discloses methods of making transgenic mice in which the mice lack endogenous heavy chains, and express an exogenous immunoglobulin locus comprising one or more xenogeneic constant regions.

Using a transgenic animal described above, an immune response can be produced to a selected antigenic molecule, and antibody producing cells can be removed from the animal and used to produce hybridomas that secrete human-derived monoclonal antibodies. Immunization protocols, adjuvants, and the like are known in the art, and are used in immunization of, for example, a transgenic mouse as described in WO 96/33735. The monoclonal antibodies can be tested for the ability to inhibit or neutralize the biological activity or physiological effect of the corresponding protein. See also Jakobovits et al., *Proc. Natl. Acad. Sci. USA*, 90:2551 (1993); Jakobovits et al., *Nature*, 362:255-258 (1993); Bruggermann et al., *Year in Immuno.*, 7:33 (1993); Mendez et al., *Nat. Genet.* 15:146-156 (1997); and U.S. Pat. No. 5,591,669, U.S. Pat. No. 5,589,369, U.S. Pat. No. 5,545,807; and U.S Patent Application No. 20020199213. U.S. Patent Application No. and 20030092125 describes methods for biasing the immune response of an animal to the desired epitope. Human antibodies may also be generated by in vitro activated B cells (see U.S. Pat. Nos. 5,567,610 and 5,229,275).

Antibody Production by Phage Display Techniques

The development of technologies for making repertoires of recombinant human antibody genes, and the display of the encoded antibody fragments on the surface of filamentous bacteriophage, has provided another means for generating human-derived antibodies. Phage display is described in e.g., Dower et al., WO 91/17271, McCafferty et al., WO 92/01047, and Caton and Koprowski, *Proc. Natl. Acad. Sci. USA*, 87:6450-6454 (1990), each of which is incorporated herein by reference in its entirety. The antibodies produced by phage technology are usually produced as antigen binding fragments, e.g. Fv or Fab fragments, in bacteria and thus lack effector functions. Effector functions can be introduced by one of two strategies: The fragments can be engineered either into complete antibodies for expression in mammalian cells, or into bispecific antibody fragments with a second binding site capable of triggering an effector function.

Typically, the Fd fragment ($V_H$-$C_H1$) and light chain ($V_L$-$C_L$) of antibodies are separately cloned by PCR and recombined randomly in combinatorial phage display libraries, which can then be selected for binding to a particular antigen. The antibody fragments are expressed on the phage surface, and selection of Fv or Fab (and therefore the phage containing the DNA encoding the antibody fragment) by antigen binding is accomplished through several rounds of antigen binding and re-amplification, a procedure termed panning. Antibody fragments specific for the antigen are enriched and finally isolated.

Phage display techniques can also be used in an approach for the humanization of rodent monoclonal antibodies, called "guided selection" (see Jespers, L. S., et al., *Bio/Technology* 12, 899-903 (1994)). For this, the Fd fragment of the mouse monoclonal antibody can be displayed in combination with a human light chain library, and the resulting hybrid Fab library may then be selected with antigen. The mouse Fd fragment thereby provides a template to guide the selection. Subsequently, the selected human light chains are combined with a human Fd fragment library. Selection of the resulting library yields entirely human Fab.

A variety of procedures have been described for deriving human antibodies from phage-display libraries (See, for example, Hoogenboom et al., *J. Mol. Biol.*, 227:381 (1991); Marks et al., *J. Mol. Biol*, 222:581-597 (1991); U.S. Pat. Nos. 5,565,332 and 5,573,905; Clackson, T., and Wells, J. A., *TIBTECH* 12, 173-184 (1994)). In particular, in vitro selection and evolution of antibodies derived from phage display libraries has become a powerful tool (See Burton, D. R., and Barbas III, C. F., *Adv. Immunol.* 57, 191-280 (1994); and, Winter, G., et al., *Annu. Rev. Immunol.* 12, 433-455 (1994); U.S. patent application no. 20020004215 and WO92/01047; U.S. patent application no. 20030190317 published Oct. 9, 2003 and U.S. Pat. No. 6,054,287; U.S. Pat. No. 5,877,293. Watkins, "Screening of Phage-Expressed Antibody Libraries by Capture Lift," Methods in Molecular Biology, Antibody Phage Display: *Methods and Protocols* 178: 187-193, and U.S. Patent Application Publication No. 20030044772 published Mar. 6, 2003 describes methods for screening phage-expressed antibody libraries or other binding molecules by capture lift, a method involving immobilization of the candidate binding molecules on a solid support.

Useful embodiments of the invention include, but are not limited to, the following:

Embodiment 1

A recombinant expression vector, comprising an expression cassette comprising a hamster GAPDH promoter, operably linked to an exogenous gene of interest, further comprising a regulatory element that
  (a) comprises a nucleic acid sequence that is at least 95% identical to the nucleic acid sequence set forth in SEQ ID NO:35 or to the nucleic acid sequence set forth in SEQ ID NO:38; and
  (b) is operably linked to the promoter.

Embodiment 2

The recombinant expression vector of Embodiment 1, wherein the GAPDH promoter comprises the nucleotide sequence of SEQ ID NO:50, or an operable fragment thereof.

Embodiment 3

The recombinant expression vector of any of Embodiments 1-2, comprising, 3' to the GAPDH promoter and 5' to the gene of interest, the nucleotide sequence of SEQ ID NO:52.

Embodiment 4

The recombinant expression vector of any of Embodiments 1-3, wherein the regulatory element comprises a nucleic acid sequence at least 98% identical to SEQ ID NO:35 or to SEQ ID NO:38.

Embodiment 5

The recombinant expression vector of any of Embodiments 1-4, wherein the regulatory element comprises a nucleic acid sequence at least 99% identical to SEQ ID NO:35 or to SEQ ID NO:38.

Embodiment 6

The recombinant expression vector of any of Embodiments 1-5, wherein the regulatory element comprises the nucleic acid sequence of SEQ ID NO:35.

Embodiment 7

The recombinant expression vector of any of Embodiments 1-5, wherein the regulatory element comprises the nucleic acid sequence of SEQ ID NO:38.

Embodiment 8

The recombinant expression vector of any of Embodiments 1-7, wherein the regulatory element is in the plus orientation.

Embodiment 9

A mammalian host cell comprising the recombinant expression vector of any of Embodiments 1-8.

Embodiment 10

The mammalian host cell of Embodiment 9, wherein the cell is a CHO cell.

For example, certain useful embodiments of the invention include the recombinant expression vector, comprising an expression cassette comprising a hamster GAPDH promoter comprising the nucleotide sequence of SEQ ID NO:50, or an operable fragment thereof, operably linked to an exogenous gene of interest, and 3' to the GAPDH promoter and 5' to the gene of interest, the nucleotide sequence of SEQ ID NO:52; and the expression vector further comprises a regulatory element that (a) comprises a nucleic acid sequence that is at least 95%, 96%, 97%, 98%, 99%, or 100% identical to the nucleic acid sequence set forth in SEQ ID NO:35 or is at least 95%, 96%, 97%, 98%, 99%, or 100% identical to the nucleic acid sequence set forth in SEQ ID NO:38; and (b) is operably linked to the promoter. Such embodiments include those in which the regulatory element is in the plus orientation and embodiments in which the regulatory element is in the minus orientation.

The invention will be more fully understood by reference to the following examples. These examples are not to be construed in any way as limiting the scope of this invention.

EXAMPLES

Example 1: Materials and Methods

Figure 1:
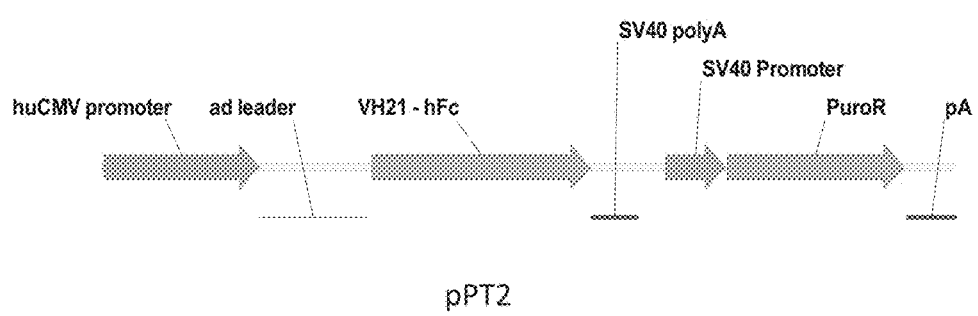
FIG. 1 is a schematic representation of the expression cassettes contained on the pPT1 and pPT2 stable expression vector. Not shown is the vector backbone which contains sequences which do not impact the results presented here.

We desired a mammalian expression vector for stable pool generation that contained separate expression and selection cassettes in order to speed the time to stable pool recovery while maintain reasonable levels of protein expression over a several month period. We started with 2 vectors (pPT1 and pPT2; see FIG. 1) that contains huCMV promoter and adenovirus tripartite leader for mammalian expression, upstream of the gene of interest, which in these studies is a reporter gene human Fc, derived from the constant region of the heavy chain of human IgG1 and is preceded by the VH21 signal peptide. The pPT1PuroR selection cassette contains a weak Kozak consensus sequence (CGGCCC) preceding PuroR. In the vector pPT2 this was optimized to the consensus strong Kozak sequence (GCCACC). Note the vector configurations represented in the drawings represent the critical regulatory elements and expression cassettes on the vector. Not shown are the vector backbone elements which do not effect the expression in mammalian cells.

Cell Culture.

pPT vectors expressing human Fc were used to generate stable cell pools in CHO-S cells (Invitrogen). CHO-S parental cells were maintained in CD-CHO medium (Invitrogen) supplemented with 8 mM L-glutamine and were transfected with 4 µg of linearized plasmid DNA using a Lipofectamine LIPOFECTAMINE® LTX transfection kit (Invitrogen) according to the manufacturer's instructions. Two days after transfection, the pools were resuspended in selection media containing 10 µg/mL puromycin. Every 2-3 days until recovery, viable cell density and viability were monitored using a VI-CELL® counter (Beckman Coulter) and media was exchanged. Recovery was defined as >90% viability by VI-CELL®.

As described above, vectors were linearized and transfected into CHO-S cells. Cells were selected with puromycin and recovered stable CHO-S cell lines were immediately used to seed 4-mL batch productions in 24-well deep well blocks at 1 million viable cells/mL in production medium. The conditioned media (CM) from these batch productions was used to determine titer by ForteBio OCTET® Red; productions were harvested by centrifugation after six days and huFc titers were measured using a ForteBio OCTET® Red equipped with Protein A biosensors and calculated employing a huFc calibration curve. To assess the stability of expression, the stable pools were passaged two times per week for various lengths of time, and then the batch production procedure was repeated using the older stable pools.

Results (The poor Kozak sequence preceding PuroR in pPT1 resulted in increased the selection stringency of puromycin selection. Therefore recovery of cells transfected with pPT1 was variable and sometimes did not survive puromycin selection and increased variability of titers was observed. When the Kozak was optimized, transfected CHO-S containing pPT2 did recover more constantly. We proceeded using the pPT2 vector for subsequent vector modification.

Example 2: Cloning of Hamster GAPDH Promoter, Exons and Introns into Vectors

The hamster GAPDH gene locus was cloned from CHO-K1 genomic DNA. We consulted the published hamster GAPDH genomic sequence within NCBI (NW_003613610.1). PCR primers were designed so that the fragment would include the hamster GAPDH promoter, the first and second exons and introns as well as a small portion of exon 3 including the splice acceptor. We determined the sequence of the amplified product and used the annotation of the mouse (NM_008084) and hamster (NM_001244854) GAPDH transcripts published within NCBI to annotate the hamster sequence including exon/intron boundaries.

Figure 2:
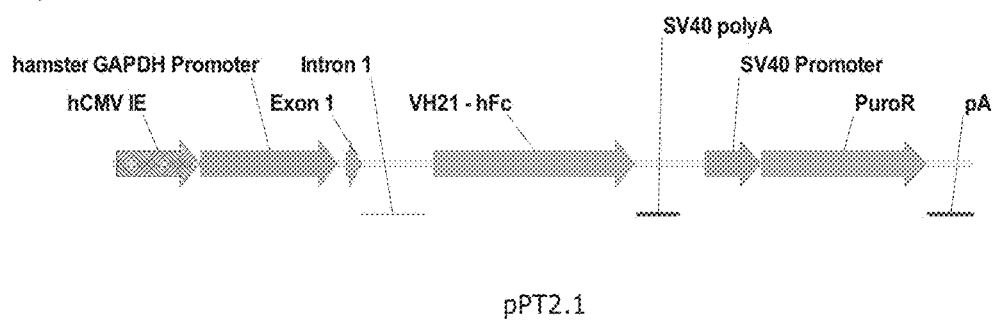
FIG. 2 is a schematic representation of the expression cassettes contained on the pPT2.1 stable expression vector. Not shown is the vector backbone which contains sequences which do not impact the results presented here.

From the sequenced hamster GAPDH gene locus, we identified the core hamster GAPDH promoter, the first exon and intron, and the second exon splice acceptor. These were cloned in lieu of the human CMV core promoter within pPT2, generating pPT2.1 (FIG. 2).

Figure 4:
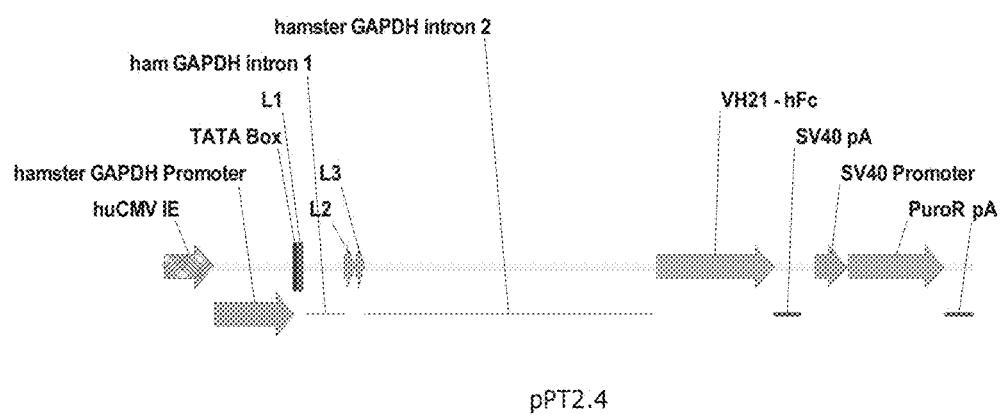
FIG. 4 is a schematic representation of the expression cassettes contained on the pPT2.4 stable expression vector. Not shown is the vector backbone which contains sequences which do not impact the results presented here.

We also determined from the sequenced hamster GAPDH gene locus (SEQ ID NO:11), the second hamster GAPDH exon and intron plus the third exon splice acceptor from the sequenced hamster GAPDH gene locus. In both the hamster and mouse transcripts, the start codon for GAPDH protein resides within exon 2. When we cloned the second GAPDH intron into pPT2.1, we made sure to abolish this translational initiation site. pPT2.4 incorporates the adenovirus tripartite leader, and both first and second hamster GAPDH introns plus exon sequences (FIG. 4).

In more detail, CHO-K1 cells (5 million in log phase growth) were harvested and used to extract CHO-K1 genomic DNA using a Qiagen DNEASY® Blood and Tissue Kit. Primers were designed to amplify an approximately 4-kb fragment from the hamster GAPDH gene locus, containing the hamster GAPDH promoter, as well as the first 2 exons and introns of hamster GAPDH using forward primer 5'-CTA CCC AGA GAC CTA TTT CTG TCA TAG CC 3'//SEQ ID NO:9 and reverse primer 5'-CCA GGC GTC CAA TAC GGC C-3'//SEQ ID N:10. The resulting PCR product was gel purified and TOPO cloned using Invitrogen's pCR4-TOPO blunt kit (Life Technologies) according to the manufacturer's instructions. Positive clones were subjected to sequencing for sequence confirmation.

The confirmed nucleic acid sequence for hamster (*Cricetulus griseus*) GAPDH genomic fragment was the following (−2049 through +2161 relative to transcription start site):
CTACCCAGAGACCTATTTCTGTCATAGC-CTTTTGGGACACATAA AGCTTCCTTCCTGCATA-GAACACCCCACAACAGTGTATCAGGAGTGTACAA GTTGACAAACAATGCTCTAGACCTACGGTTTTCT-TCCTCTGTGTGCCTCATC CCAGAAGAGATCAT-GACTCCCAGGAGTCAGCCTTTACTATGGGTCT-GCAG GGGCGTCCAGCCCCTCAGCGGCAAGCCATGC-CCACCCTCCCCAAGTCCTTA ATCTGCTGAGTCACT-TGGAACAGGAGACACTGATTCTGCTGTCAT-GACAAC AGCACATTGCCATAGAAATGCTCCCTACCTCT-TACGTGTGTGGTGGGGGAA CAGTAATGACAAAC-CATAGGCAGGAGGCAAAAGGGAAGACGGCAC-CTCAG AAACATGTGTTAGGTTAGGGCAGAACTATG-GAGGGGCTCCTGAGACTCTTT GATGGGAAAGGGT-TAATGCTGCTCCTGAAACCTCTGTTGGAAGGCA-GAAAA GGGACAGGGCTGAGTCCCCGCACTGGGAC-CATTTCCATCCTCTGCATCCTG CCCCCGGCTCATG-GAAAGCCTGGGCATGGGCCACACAGCTGTCA-GTCTTGG CTCTGGGGCCCCAAGGAGGTAGGGCAATCCCA-GAATGGCAAGGAGCCAGG ACTGGATTTGGGGT-GCAGCCCAGCCTGCTCCCTGCCTTT-TAAGCAAAGGTT ATCACCAGGCCAGCTAAACTTAGCAATTAGGCTCT-TCAGCTAAAAGAGCAG GGGGCTGGTCTCAAGTTG-CACTGACCTAGCAAAGAGGCCCCAGGATCCCCC TGCCCAGCACCTGTGGCTGAGCTCCCAAGCCCTTC-CCGAGAGCTCAGGATC CACCCTTTCCACCCTC-CCTACTCTTCAGAGGAGGAACCCCCTTTCTCCTTCC CACTTGTTGGAGGGGGCTGGGGCCAGGCTGT-TCTGGCTTGGGGTATAATAC CCCCTACCCCTTC-TACTTTCCCCTCCTCTCAGACCTCACCCTGCCTC-CACGA GGGCAGCCAAGAAAGGAGAGTCCCTGGCTGCA-GGGCCAGTAGGCACGTCC CAG-GACGGGGAGGGACTTCCGCCCTCACGTCCA-GCTCTCCGCCCTGGGGCT GCAGTGGGTGAAAGGGGCAGTGTCTCCTAGC-CTGGGCGGTGCAACCCTCAG GTTCCGAGGAG-GAACGCTCTGGGAGGCTTCTTTGCCTCCTCCAAC-CCAACC CACAACCAGGACATTGTCCTCACCCCGGGGC-CCCAACCTAGACCTTAACTG AGGAACACAGAGGC-CAGTTTGTAAGTCTCAATTATGCAGGGCATC-CCGACC TGTGGCGTAGGGAGCGCCCCTCCAGGCCGCTTC-CCTAGCCTCCTCCTGGCCC TCACAGCCCAGGC-CTCTGGCCCAAGAAATG-GAAGTGGGGGTGGGGGATGG AACTGCGAATGCGAAGGGCCCCCGCAGGAG-GCAAAGTGACCCCTCCCGGG CCTTTTCTGCTC-CGAGACTTGTTTTTGCCTGTGTCACTAC-CGAAGAACCACG AGAAGATCCTCAACTTTTCCACAGCCTTTG-CATAAAGGGGAGAGGGTCGGC GGTGCAGCTGTG-GCACACACGCACTTCTGCTCAACCCGC-CCCCCCCGCCC CCGTTCCTGTTCCTTCCCAGGTTCTCCCCATTT-TATCGGGGCGGCAACTTTTA GGTCCCTGGGTCCTG-GAAGTCCTTAGTACACACTCTTCGTCCTTAAGTC-CAT AGTCTGTATTCCCTCGGTCCTATCCTGTCCCCCAT-CACCGGGTCACCTCCCC AGCGAAGCAATCTCAGT-TCCCCTCCCCCTCTCAGCCCCGAGCCCACACGTTT GGTGCGTGCACATTTCAAAAACGAGGCGGGTC-CAAAGAGAGGGGGTGGGG AGGTGCCGAGTGGC-CCAGCTACTCGCGGCTTTACGGGTGCACG-TAGCTCAG GCCTCAGCGCCCTTGAGCTGTGACTGGATGGAT-GAGCGGGGCGGGAGGCG GGGCGAGCGTCCTCG-GCGCTCCCCACCACCCCAGTTCCTATAAATACGGAC TGCAGCCCTCCCCGGTGCTCTCTGCTCCTCCCTGT-TCTAGAGACAGCCGCAT CTTTCCGTGCAGTGCCA-GGTGAAAACCGCAGAGTGGGCCGCAGGTGGCCGG GGACGGTCGGAAACGGGGAAGGGGGGCGCTCAGCCCGGGACTGCGGGCGC TGGGGCGAGCTCCACTGCCCGAGCCCGGGCTCCGCATTGCAGAGGCTGGAG
GGGGACGTGATGGGGCGCGCGGCGGGAATGGAGGCGGGGGGGGGGGTCG CCCTGTGACCGTGGTCCACGCTGACCTCTCTTTCTTCTCTCTCCCTCCGCAGC
CTCGCTCCGGAGACGCAATGGTGAAGGTCGGCGTGAACGGGTGAGTTCGTG
GCTGGGCTAGGGTGGGGCTCCGGGTCCCGCTCCGTCGCGTATGCAGGTCTA CCCCACCCCGGGGCTCTGCGGGAGCGTGGGGTGGCCGGTGGGTGGCCGCA
GCACCCAAGGAGACCTCAAGGTCAGCGAGCCGGCTCCGCCCTTGCGGGGAT GAGCAGCGCGGAGTCCTCACGAGGAGGACCATCCCCGCGCGCACGCATGCTTAGGCTCCATCCCGATCCCCAGCCGGGGGCTTCTTTCTTTACTTTCGCGC CCTGAGGAACCACGTGCCAGACGGGAGCCCCTCCCCCATTGCCCTCTACCC
CCCCCCCCGCGCGCGCCTCCAGGTCGGTGGCACCGGGCCGTGCGGTGCCCG CTTTAGCGCATCCATCATCTCCCAAGGGCTTCCTTTAGGGTGGCTGGCCGCC
GCCATGTTGCAAACGGGAAGGAAATGAATGAACCACCGTTAGGAAACCTC CCTTCGGCCTTCCTCCTTCCTAGCCCGTGACTAACCTCCCCACTCCCTCCCCGGGTGGAGTCGCCTCTGTACTGTAAGCCAGGTGATGCAAGGCTTCCGTGCT CTCGAGAGAGCTCTACCTCGCCAGCTGTCTCATATTATTAGCCTCAAAGCAGCCCTCAAGCCTCATTTACCTTGAGCATATGATATATTTTGTAGATTCTCTG AGAATCGAAGCGGACTTGGAGAGGTCTGCTTGTCCTTCTCCCAGCCCAAAGGTGGTAGCTATGGCGTAGCGCCGAGGGGGGAGTGGGGGGGGAGCTGAGT CATGGTGGTTCTGAAAAGAAAATTTCCACCACAAAATGGCTCCGGTGCTAG
CATCCCCTTCCCCCCATAACCTCTGCTTCCCATCACACCCTGACCCAAACCC TGTAGGCCAGACTGTAAAGGTCACTAAGAGGATTGAGTGTCTGAGCCTCGG
AACCCTGCCCTTCTCCCCATCCCATCCTCTGGAAACCAGATCTCCCCCGCTC CACCCTAATCTGAGGTTATATTTAGCCGGCTGACCTTTCAGTATTTGGGGTC
TGGGCCCCTACACACATCTGTTGCTCCTGCTCCTGATTTTTAGCTAGCAAAT TCAAGTGCTTTGCAAATTAGAGCCCAGGGATTAGGGGTTGGAAAGCTCAGT
GGTTTTCTCAGTCTTTCCCTTTAGGGGGAGGGACTTGGAGGAAGCAGGTGG GCCGACCCCTGTCCTACTCATTCTGACCTTTAACCTTGCCCTTTGAGCTTGATGATGCTGAGTGCACGAGTTCTTCCTGTCCAGGGGGTGTAGCCTGAAGCCA GGCCAGGCTAGAACAAACTTCCCAGGGGGTGGGGGTAGTGAATGCCTTGTG
CCCACACAGGGGCACACTGCCACCTCTTGGAGACTTGAAATGACTGGTGGG GGGGTTGGACAAGGCTTTGAGCCCAATCACCTCTTGGACAGGAAAGTAACC
CCCACTTTATGGCCCTGCTGTAAAAGCCCAGTCAAACCTCATTTGTCCAAGG AAGATAGACCTCTTGGGGCTTCCTAAGGATAGGGGTGTTCTATATTTGGGC
CCTGCTTCTAAGCATTCAGCCAGCTTTATTAAAGGAAATTCATAACAAAACT TGAATTTCCTGCTTCTTAAATACTAATAGTGTGCTGGATCTCCATTAAAAAT
GCTGTCTTGCACAGTAGGCTATGGTTTCTGTGGGCTCTCTACAGCTATGGGA CAACTGGATTCTGTTTTCTGAAGGGCATGTGTCAGCTCAGTACTGACTATAG
ACCTATGAGTTCTCTGACCCCCTAACTCACCTTTTTTTTTCTTGCCTCAGATT TGGCCGTATTGGACGCCTGG//SEQ ID NO:11. Vector pPT2.1 incorporates portions of the hamster GAPDH gene locus, including a portion of the Hamster GAPDH promoter (SEQ ID NO:11), i.e., the following portion of SEQ ID NO:11 from −532 through +305 relative to the transcription start site: ACCACGAGAAGATCCTCAACTTTTCCACAGCCTTTGCATAAAGGGGAGAGG GTCGGCGGTGCAGCTGTGGCACACACGCACTTCTGCTCAACCCGCCCCCCC
CCGCCCCCGTTCCTGTTCCTTCCCAGGTTCTCCCCATTTTATCGGGGCGGCA ACTTTTAGGTCCCTGGGTCCTGGAAGTCCTTAGTACACACTCTTCGTCCTTA
AGTCCATAGTCTGTATTCCCTCGGTCCTATCCTGTCCCCCATCACCGGGTCA CCTCCCCAGCGAAGCAATCTCAGTTCCCCTCCCCCTCTCAGCCCCGAGCCCA
CACGTTTGGTGCGTGCACATTTCAAAAACGAGGCGGGTCCAAAGAGAGGG GGTGGGGAGGTGCCGAGTGGCCCAGCTACTCGCGGCTTTACGGGTGCACGT
AGCTCAGGCCTCAGCGCCCTTGAGCTGTGACTGGATGGATGAGCGGGGCGG GAGGCGGGGCGAGCGTCCTCGGCGCTCCCCACCACCCCAGTTCCTATAAAT
ACGGACTGCAGCCCTCCCCGGTGCTCTCTGCTCCTCCCTGTTCTAGAGACAG CCGCATCTTTCCGTGCAGTGCCAGGTGAAAACCGCAGAGTGGGCGCAGGT
GGCCGGGGACGGTCGGAAACGGGGAAGGGGGGCGCTCAGCCCGGGACTGC GGGCGCTGGGGCGAGCTCCACTGCCCGAGCCCGGGCTCCGCATTGCAGAGG
CTGGAGGGGGACGTGATGGGGCGCGCGGCGGGAATGGAGGCGGGGGGGG GGGTCGCCCTGTGACCGTGGTCCACGCTGACCTCTCTTTCTTCTCTCTCCCTC CGCAGCCTCGCTCCGGAG//SEQ ID NO:49; the first exon and intron; and the splice acceptor of the second exon into pPT2. First, the vector portion of pPT2 was digested by XbaI and SalI and gel purified, excising the whole CMV promoter from pPT2. The CMV IE enhancer was replaced by a PCR product using Forward Primer 5 (5'-TGA AGT CTG GAT CCG TTA CAT AAC TTA CGG TAA ATG GC-3'//SEQ ID NO:14) and Reverse Primer 5 (5'-CCA TGG TAA TAG CGA TGA CTA ATA C-3'//SEQ ID NO:15), and finally, the GAPDH promoter including exon1 and intron1 was incorporated by a PCR product using Forward Primer 6 (5'-GTC ATC GCT ATT ACC ATG GCC TCG AGA CCA CGA GAA GAT CCT CAA C-37/SEQ ID NO:16) and Reverse Primer 6 (5'-CAT TCC ATG GTG GCC TAG TCG ACG CTA GCC TCC GGA GCG AGG CTG-37/SEQ ID NO:17). The templates for these PCR reactions were pPT2, pPT2 and pCR4-GAPDH genomic fragment respectively. All 3 PCR products were cloned into the XbaI and SalI linearized vector portion of pPT2 by SLIC.

Vector pPT2.4 incorporates the second hamster GAPDH intron into pPT2.1 (FIG. 4); however, first an intermediate construct pPT2.2 was generated. In pPT2.2, the pPT2.1 sequence from the GAPDH TATA box and extending to the exon 2 splice acceptor was replaced by the CMV TATA, the adenovirus tripartite leader and Major Late Enhancer (MLE) as they are found in the starting vector and pPT1. In short, pPT2.1 was digested with BamHI and SalI and the vector portion was gel purified. To replace the excised hCMV IE and GAPDH Promoter, a PCR product using Forward Primer 5 (SEQ ID NO:14) and Reverse Primer 7 (5'-CGA GCT CTG CTT ATA TAG GAA CTG GGG TGG TGG-37/ SEQ ID NO:18) and template pPT2.1 was combined with a PCR product using Forward Primer 7 (5'-GTT CCT ATA TAA GCA GAG CTC GTT TAG TGA AC-3'//SEQ ID NO:19) and Reverse Primer 8 (5'-CAT TCC ATG GTG GCC TAG TCG ACG CTA GCA GGT TTT CCG ATC CGG TC-37/SEQ ID NO:20) also using pPT1 as a template. These PCR products were cloned into the BamHI and SalI digested vector portion of pPT2.1 by SLIC.

A second intermediate, pPT2.3 was created, whereby the adenovirus MLE, which is embedded as an intron between leaders 1 and 2 (L1 and L2) of the adenovirus tripartite leader (TPL), was excised and replaced by the GAPDH intron1. Three PCR products were cloned into the BamHI and SalI digested vector portion of pPT2.1 by SLIC. The first PCR product encompassed the hCMV IE, GAPDH Promoter, and including the sequence up until the $1^{st}$ leader (L1) of the TPL. These were amplified using Forward Primer 5 (SEQ ID NO:14) and Reverse Primer 9 (5'-CGG TAC TCA CCC CAA CAG CTG GCC CTC-37/SEQ ID NO:21). The second PCR product used the GAPDH intron 1 as a template and was amplified by PCR using Forward Primer 8 (5'-CTG TTG GGG TGA GTA CCG CAG AGT GGG CC-3'//SEQ ID NO:22) and Reverse Primer 10 (5'-CCG CGA GCT GCG GAG GGA GAG AGA AG-37/SEQ ID NO:23). Lastly, the third PCR product amplified L2 and L3 of the TPL using Forward Primer 9 (5'-CCT CCG CAG CTC GCG GTT GAG GAC AAA C-37/SEQ ID NO:24) and Reverse Primer 8 (SEQ ID NO:20).

Finally, pPT2.4 was derived from the intermediate construct pPT2.3. Plasmid pPT2.4 has the $2^{nd}$ intron including exon/intron boundaries added to pPT2.3. Plasmid pPT2.4 incorporates the hamster GAPDH promoter, i.e., the following portions of SEQ ID NO:11

(i) from -532 through -23 bp relative to the transcription start site:
(SEQ ID NO: 50)
ACCACGAGAAGATCCTCAACTTTTCCACAGCCTTTGCATAAAGGGGAGAG

GGTCGGCGGTGCAGCTGTGGCACACACGCACTTCTGCTCAACCCGCCCCC

CCCCGCCCCCGTTCCTGTTCCTTCCCAGGTTCTCCCCATTTTATCGGGGC

GGCAACTTTTAGGTCCCTGGGTCCTGGAAGTCCTTAGTACACACTCTTCG

TCCTTAAGTCCATAGTCTGTATTCCCTCGGTCCTATCCTGTCCCCCATCA

CCGGGTCACCTCCCCAGCGAAGCAATCTCAGTTCCCCTCCCCCTCTCAGC

CCCGAGCCCACACGTTTGGTGCGTGCACATTTCAAAAACGAGGCGGGTCC

AAAGAGAGGGGGTGGGGAGGTGCCGAGTGGCCCAGCTACTCGCGGCTTTA

CGGGTGCACGTAGCTCAGGCCTCAGCGCCCTTGAGCTGTGACTGGATGGA

TGAGCGGGGCGGGAGGCGGGCGAGCGTCCTCGGCGCTCCCCACCACCCC

AGTTCCT ATA//;

(ii) Intron 1 from +64 through +293:
(SEQ ID NO: 51)
ACCGCAGAGTGGGCCGCAGGTGGCCGGGGACGGTCGGAAACGGGGAAGGG

GGGCGCTCAGCCCGGGACTGCGGGCGCTGGGGCGAGCTCCACTGCCCGAG

CCCGGGCTCCGCATTGCAGAGGCTGGAGGGGGACGTGATGGGGCGCGCGG

CGGGAATGGAGGCGGGGGGGGGGGTCGCCCTGTGACCGTGGTCCACGCTG

ACCTCTCTTTCTTCTCTCTCCCTCCGCAGCC//;
and (iii) Intron 2 from +334 through +2145:
(SEQ ID NO: 52)
GTGAGTTCGTGGCTGGGCTAGGGTGGGGCTCCGGGTCCCGCTCCGTCGCG

TATGCAGGTCTACCCCACCCCGGGGCTCTGCGGGAGCGTGGGGTGGCCGG

TGGGTGGCCGCAGCACCCAAGGAGACCTCAAGGTCAGCGAGCCGGCTCCG

CCCTTGCGGGGATGAGCAGCGCGGAGTCCTCACGAGGAGGACCATCCCCC

GCGCGCACGCATGCTTAGGCTCCATCCCGATCCCCAGCCGGGGGCTTCTT

TCTTTACTTTCGCGCCCTGAGGAACCACGTGCCAGACGGGAGCCCCTCCC

CCATTGCCCTCTACCCCCCCCCCGCGCGCGCCTCCAGGTCGGTGGCACC

GGGCCGTGCGGTGCCCGCTTTAGCGCATCCATCATCTCCCAAGGGCTTCC

TTTAGGGTGGCTGGCCGCCGCCATGTTGCAAACGGGAAGGAAATGAATGA

ACCACCGTTAGGAAACCTCCCTTCGGCCTTCCTCCTTCCTAGCCCGTGAC

TAACCTCCCCACTCCCTCCCCGGGTGGAGTCGCCTCTGTACTGTAAGCCA

GGTGATGCAAGGCTTCCGTGCTCTCGAGAGAGCTCTACCTCGCCAGCTGT

CTCATATTATTAGCCTCAAAGCAGCCCTCAAGCCTCATTTACCTTGAGCA

TATGATATATTTTGTAGATTCTCTGAGAATCGAAGCGGACTTGGAGAGGT

CTGCTTGTCCTTCTCCCAGCCCAAAGGTGGTAGCTATGGCGTAGCGCCGG

AGGGGGGAGTGGGGGGGAGCTGAGTCATGGTGGTTCTGAAAAGAAAATT

TCCACCACAAAATGGCTCCGGTGCTAGCATCCCCTTCCCCCCATAACCTC

TGCTTCCCATCACACCCTGACCCAAACCCTGTAGGCCAGACTGTAAAGGT

CACTAAGAGGATTGAGTGTCTGAGCCTCGGAACCCTGCCCTTCTCCCCAT

CCCATCCTCTGGAAACCAGATCTCCCCCGCTCCACCCTAATCTGAGGTTA

TATTTAGCCGGCTGACCTTTCAGTATTTGGGGTCTGGGCCCCTACACACA

TCTGTTGCTCCTGCTCCTGATTTTTAGCTAGCAAATTCAAGTGCTTTGCA

AATTAGAGCCCAGGGATTAGGGGTTGGAAAGCTCAGTGGTTTTCTCAGTC

TTTCCCTTTAGGGGGAGGGACTTGGAGGAAGCAGGTGGGCCGACCCCTGT

CCTACTCATTCTGACCTTTAACCTTGCCCTTTGAGCTTGATGATGCTGAG

TGCACGAGTTCTTCCTGTCCAGGGGGTGTAGCCTGAAGCCAGGCCAGGCT

AGAACAAACTTCCCAGGGGGTGGGGGTAGTGAATGCCTTGTGCCCACACA

GGGGCACACTGCCACCTCTTGGAGACTTGAAATGACTGGTGGGGGGTTG

GACAAGGCTTTGAGCCCAATCACCTCTTGGACAGGAAAGTAACCCCCACT

TTATGCCCTGCTGTAAAAGCCCAGTCAAACCTCATTTGTCCAAGGAAGA

TAGACCTCTTGGGGCTTCCTAAGGATAGGGGTGTTCTATATTTGGGCCCT

GCTTCTAAGCATTCAGCCAGCTTTATTAAAGGAAATTCATAACAAAACTT

GAATTTCCTGCTTCTTAAATACTAATAGTGTGCTGGATCTCCATTAAAAA

-continued
```
TGCTGTCTTGCACAGTAGGCTATGGTTTCTGTGGGCTCTCTACAGCTATG

GGACAACTGGATTCTGTTTTCTGAAGGGCATGTGTCAGCTCAGTACTGAC

TATAGACCTATGAGTTCTCTGACCCCCTAACTCACCTTTTTTTTCTTGC

CTCAGATTTGGC//.
```

Using pPT2.3 as a template, the promoter region was amplified with primers Forward Primer 5 (SEQ ID NO:14) and Reverse Primer 11 (5'-GAA CTC ACC TGA GGT TTT CCG ATC CGG TC-3'//SEQ ID NO:25). The GAPDH intron 2 sequence (SEQ ID NO:52) was amplified using Forward Primer 10 (5'-CGG AAA ACC TCA GGT GAG TTC GTG GCT G-3'//SEQ ID NO:26) and Reverse Primer 12 (5'-CAT TCC ATG GTG GCC TAG TCG ACG CTA GCC AAA TCT GAG GCA AGA AA-3'//SEQ ID NO:27). These PCR products were cloned into the BamHI and SalI digested vector portion of pPT2.1 by SLIC.

Vectors pPT2, pPT2.1 and pPT2.4 were linearized and transfected into CHO-S cells. Cells were selected with puromycin and recovered stable CHO-S cell pools were immediately used to seed 4-mL batch productions. The conditioned media (CM) from these batch productions was used to determine titer by ForteBio OCTET® Red, as described in Example 1.

Results: Many current expression vectors contain hybrid promoters made up of the CMV immediate early enhancer followed by a house keeping gene promoter, for example GAPDH, Elongation Factor alpha (EF1a) or chicken beta Actin (CAG) (See, e.g., Magnusson et al., Sustained, high transgene expression in liver with plasmid vectors using optimized promoter-enhancer combinations, Journal of Gene Medicine 13(7-8):382-391 (2011); Xu et al., Optimization of transcriptional regulatory elements for constructing plasmid vectors, Gene. 272(1-2):149-156 (2001)). Our subsequent efforts centered on improving CHO expression vectors by replacing the core CMV promoter with such a hybrid promoter. We chose to replace the CMV core promoter with a hamster housekeeping promoter. For our purposes we selected the hamster GAPDH gene locus to investigate it's feasibility as a hybrid promoter partner.

Figure 3:
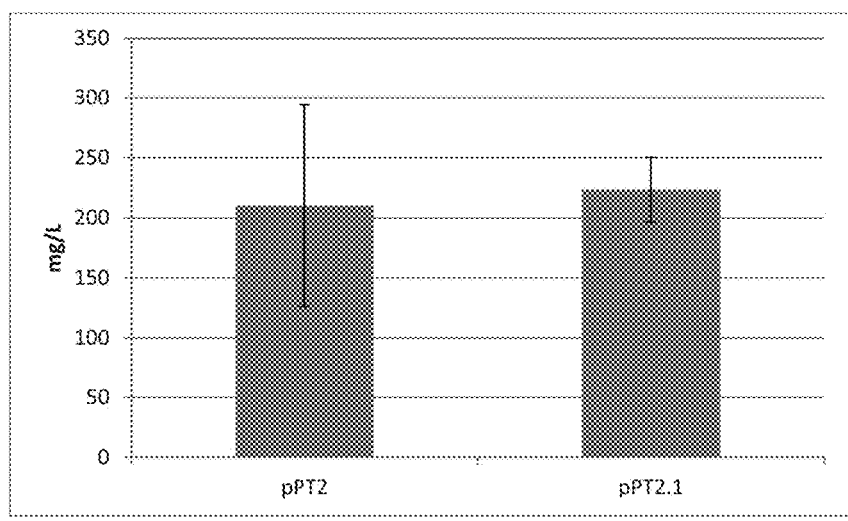
FIG. 3 shows a summary of CHO-S stable expression pool titers derived from transfection and selection with pPT2 and pPT2.1. Cells stably expressing these vectors were seeded at 1E6 cells/ml in a 24 well deep well plate. Conditioned medium (CM) was harvested 6 days later. Titers of human Fc protein in CM (reported as mg/L) were determined by ForteBIO OCTET® Red and ranges are shown from triplicate transfections from 2 separate experiments.

With the replacement of the CMV core promoter with the hamster GAPDH promoter and intron 1 (pPT2.1) we show that this vector configuration give comparable expression levels in CHO-S pools to the pPT 2 vector containing the CMV core promoter, suggesting that the hamster GAPHD promoter configured with the CMV enhancer is very active in CHO cells (FIG. 3).

Figure 5:
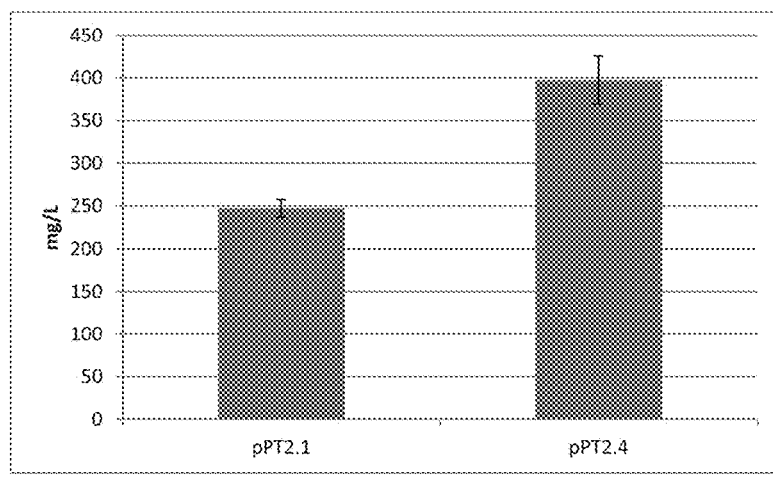
FIG. 5 shows a summary of CHO-S stable expression pool titers derived from transfection and selection with pPT2.1 and pPT2.4. Cells stably expressing these vectors were seeded at 1E6 cells/ml in a 24 well deep well plate.

Housekeeping promoters like EF1 alpha as well a chicken beta actin retain a large intron within the full promoter sequences. These introns contain many enhancer binding sites that result in promoter activation. The first intron within the GAPDH promoter is significantly smaller, so we hypothesized that the larger second hamster GAPDH intron would retain many more enhancer binding sites. We therefore included the first and second intron from the hamster GAPDH gene in our expression vector pPT2.4. This addition was able to raise expression levels by 40% compared to the pPT2.1 vector containing the GAPDH promoter and intron 1 alone. Therefore, like the EF1 alpha and Chicken beta actin promoter, the GAPDH promoter activity is enhanced by sequences found within one of its introns. (FIG. 5)

Since we believed that intron1 may not have a direct impact on expression levels and we were concerned about the possibility of alternative splice events with the inclusion of 2 introns within pPT2.4, vector pPT3 was generated using Forward Primer 11 (5'-GAT GTG TTG AAG TCT GGA TCC-3'//SEQ ID NO:28) and Reverse Primer 13 (5'-CAA CCG CGA GCC CAA CAG CTG GCC CTC-37/SEQ ID NO:29) and Forward Primer 12 (5'-GCT GTT GGG CTC GCG GTT GAG GAC AAA CTC-3'//SEQ ID NO:30) and Reverse 12 (SEQ ID NO:27). This removed the GAPDH intron 1 sequences and made a direct fusion of the 3 leader sequences that make up the TPL. These 2 PCR products were cloned into the BamHI and SalI digested vector portion of pPT2.1 by SLIC. Vector structure is represented schematically in FIG. 6.

Vectors pPT2, 2.4, 3, were transfected in CHO-S cells and cells were selected with puromycin and recovered stable CHO-S cell pools were immediately used to seed 4-mL batch productions. The conditioned media (CM) from these batch productions was used to determine titer by ForteBio OCTET® Red. Recovered stable CHO-S cell pools were also maintained under selection for an additional 1- and 2-month periods; 4-mL batch productions were set up and titers determined at the end of the run. pPT vectors containing the hamster GAPDH promoter were all capable in generating initial titers comparable or exceeding titers from the original CMV containing pPT2.0. However, a precipitous drop in titers was seen over longer culture times in all vectors, but the CHO pools expressing the pPT2 vector declined most rapidly, losing all expression within 2 months of culture. (FIG. 7). Removal of Intron1 from pPT2.4 had little effect on the expression titers (FIG. 7 pPT. 3 vs pPT2.4). As we had hypothesized, the sequences within intron 1 of the GAPDH promoter add little additional enhancer activity and made their inclusion less desirable.

Example 3: Cloning of Hamster Rps3 and Rps2 Genomic Regions

Methods.

Logarithmically growing CHO-K1 cells (5E6) were harvested and used to extract CHO-K1 genomic DNA using a Qiagen DNEASY® Blood and Tissue Kit. Primers were designed to amplify an approximate 3.3 Kb fragment containing the hamster Rps3 genomic region, including the promoter and first 3 exons (Forward primer, 5'-GAT TAG AAG CCA TCT TGT TAC AA-3'//SEQ ID NO:33 and Reverse primer, 5'-TAT ATA ACT CTG AAA GTG TCA ACC C-3'//SEQ ID NO:34). The PCR product was gel purified and TOPO cloned using Invitrogen's pCR4-TOPO blunt kit. Positive clones were subjected to sequencing and sequence confirmation.

The confirmed DNA sequence for hamster Rps3 genomic fragment including the regulatory element is the following:

SEQ ID NO: 35
```
GATTAGAAGCCATCTTGTTACAAATGTCAAAAGATCATTCCTGTTTTCTG

TAATACTTGTGTTTGACCATGTCTTGATCCATCTTCTGGAATTTGACATG

TTCCACACCTTATACCCTGACCTCCATCCTGACAAGATAAGATGTTCTGC

CACTGTCCTACATAACCAAAATGCCTCTTCAAATCGCCCAATCCTTGAAA

TTTCTGAGCTATATAAATTCTACTTTCTTCTATGTCCAATGCTGTTTTTT

CAAACTCCACTTTAGGGAGACAACCCTGTTTGACAGAAAATAAAACTTCC

TTAATCTAACTAAAACAATTTGGGTAATGGGCTTTACTTTTATTTGGTGG

GATTTGCACAGGGTGAATTGGAGCCCCCTGGAGATGACTGAGCCACGAAC
```

-continued
```
ACTGTAGTACAAGTTACTGAAGCAGGATTTGCTTCTGGACAAGGAGTGAT

TGCTGGTGTAGACATCGGAGTCCCTGTGAAGGGATGTCCTGTGGCCCAGA

CTTACACTTTCTGATAATCTGTCTTCAAAGCCCTGCTAGTTTATTACATT

GACAGCTCCCTTCTGGTAGCCCACCCCACTGTGAGTTCAAAAAGTTCAGA

GGTCCTGGTGCAAGTGTTTGATACCAGAAATGCTACAGGTAAGTCCATCT

TTAGGATCAGGGTTTATCTTTGTAATAAACATCATAGGATTGTAATGTTT

TAACAATGACGTGTGTGTGTGTGTGTGTGTGTGTGTGTGTGTGTGTGTGT

GTGTGTGTGTTTGTGTTTGTGTGGGGAGAGCATGCATGGGAAGGTCCTAG

GACCTAGGTTCTGTCCTTTGACCTCTGGGTGCTGGGATCGAAATCAAACA

CCTTTACCTACTAAGTCACCTGGCTGGTCCCCCAAATGAATTTCAATGAG

AGTTTTCATTAGTGTGGTCCTGAAGCTATAAGCAATAGGGTTCCAGTCTG

GGTAAACTCTGTTAGTGTATGCTTATGTCTGTGGTTTGCATCTCTTGCCT

CTTGGTTGCTCTGTTCAAAGTTTTTATTTATTTTTGAGTCGGGGCTCAT

GTAGACCAAGCTGGCTTCGAACTCGCTATGTAGTCGAGAATGACCTTGAA

TTTTTGATTCTCCAGCCTCCACCTCTCTAGTGCTGAAATCACTGGTGTGC

TCCTCCACGGTGGGGTACATTGATTGTTTTTCAGACCAGAATTAGATTTG

CACTTCCTGTTCCGCCTACACTACGGGTTGCTAGGTTACACTTCTTTTTC

TCTTTTCGCCTTTATAAACTCAAAACTTCATTTCCCATGAGCTCTTGCAA

GTGTCGCCGTTGCGTGGCGTTGCGTCGTCGTTCCGCGCCCTTTATACACA

CTTCCGCCCGCGAGCTACTTCCTTTCCTTTCGGTGGCGCGCGGCGGCAAG

ATGGCGGTGCAGATTTCCAAGAAGAGGAAGGTAAGCATTTCGGACCGGCT

CGGGGACTCGCGGCGCGTTTTAAAGCTGCCACGGTGAGACCCGCAGCTCC

GTGTCCGATCCCGGAGAGCGGCTACTGCCGCCTGGCGCTTCCGCGGGGCG

CGGATGGACGTGGATTGTGTGCTGGGCCGGCTCCGGGCTAGCTCAGTGTG

GCTGAGGAAGGGAGGAACAGACGCCTCAGTTCTGGGCCGAGGTGAACACT

GGAAGCCATCAGGCCTTTACTAGACGCTTTTGAGCGTCTCTCGGTCGCCA

GAATTAGTAACCCTATGGCATAGCTTGAGAGCGTGAGCTAATCCGGCGTC

TTTGGTAAGTGAGGTTTAGCAGTGCCGCCTCAGTTGAAAGGCTGCCGACT

ATTGGCGTGCTCCCTCGGGACCTGCAGCAAAAGCGTCCCGGACTTTTGTC

ATTTCATGGGGAAGAAGTGTGTGAAGATCATCAGGTTTAGAAATAGATGG

CCTGTCTTTGTGATCAAGCACATAGATCATAAAGCTGTTGTCCACATGCT

GTTTGGGTTAGATTTGTCCTCTCTTGCTTCAGGTACGAGTTACATACACA

CACGGTGTTCTTGCTGTGCTGTGTGAACTGCAGATGTGCTACTTGAATAG

ATTTTTGTTCTGTGTGTGTAAATGTTTTAAAACCCTTCGATGAAGAGGTG

ATGACGAGTCTGACGGAGGTGTTGTCTTTGTCCAAAAGGCGTCACTGTGC

TGCGTTCTGTGGCACAGCTGAAAGCACTATGGTCAAAGGAACTTCCTAAA

GATGACCTAGAGGCATTTGTCTGAGAAGGGTTGCTGCATTCCCGAAGGGT

CATTGGGGTCGAACTGGGTAAGCCTCTACCCTTTCTTAACTCTGAACTTG

CTTTTGGTTTAGTTTGTGGCTGATGGCATCTTCAAAGCAGAGCTGAATGA

GTTTCTCACTCGGGAACTGGCTGAAGACGGCTACTCGGGAGTTGAAGTCC
```
-continued
```
GAGTTACACCAACCAGAACAGAAATCATTATTTTAGCCACCAGGTAAAAA

TATGTTTGACTGGCTATTACCTGTAATCACTGTGTGTATTGAGTTGCTGT

GTAAACTTGGAACAACCAACCAGTGAACCTGCTCCTTTTTTGTTGTTGTT

TTTTGTTTGTTTTTTGAGACAGGGTTTCTCTGCATTGCTTGGGAGCCTGG

CCTGGAACTTGCTCTGTGGATCAGTCTGGCCTAAGACTCACAGAGATCCG

CCTGCTCTGCCTCCTGAGTGCTGGGATTAAAGGTGTGCACCACCACCACT

GCCTGGCCTTGGAGTTGCTTTTTTAAAACACCATTTGTAAAGAATTTACC

TTAATACTTTTTTAAAGTGTGTCCTTGCTGTGTGATAAATGGTATGTGAG

GTGTTGCAAATAAATTGTAATTTTCCCTTCTGCAGAACACAAAATGTTCT

TGGTGAGAAGGGTCGTCGAATCAGAGAGTTGACTGCGGTAGTTCAGAAGA

GGTTCGGCTTCCCTGAGGGCAGCGTAGAGGTGAGTTTCCCTGGTTTATAC

CAGGGGCAGTAGACTGGATTTAGAAGTTGCTTCTGTAGAACGGTAATTCT

GGACAATGAGTAGTACAGGTGGGTTGACACTTTCAGAGTTATATA//.
```

Logarithmically growing CHO-K1 cells were harvested and used to extract CHO-K1 genomic DNA using a Qiagen DNEASY® Blood and Tissue Kit. Primers were designed to amplify an approximate 3.2 Kb fragment containing the hamster Rps2 genomic region, including the promoter and first 2 exons (Forward primer, 5'-CAA AGA GGT TGA GAT CGT ACC C-3'//SEQ ID NO:36 and Reverse primer, 5'-TGA GAC CGC TGC AAA AGC-3'//SEQ ID NO:37). The PCR product was gel purified and TOPO cloned using Invitrogen's pCR4-TOPO blunt kit. Positive clones were subjected to sequencing and sequence confirmation.

The confirmed DNA sequence for hamster Rps2 genomic fragment including the regulatory element is the following:

SEQ ID NO: 38
```
CAAAGAGGTTGAGATCGTACCCACCACTCTGCAAAGGCCAAGTTAGTGTT

AAAGTCTGTCCCAAAGCACACATACCATCAAGATAACTCCATAATCATTC

TGTAGGGAGGCAGGCTACATAAAGAAACTCAAGGGCAAACCTGTGGGGGT

TGAGTCCCCCAAGATTTGCCAATATTTGACTGAAGAAGCTGGAATACCAC

CTAGAGCCTTCTGAAATGTTTTCTTGCCCCATAAAGGAACTATCATTCAT

TCGCAGAGTGAGACAGGATCGATTCCTAGACAGCTGGGCAGCTGTCTGGA

ATTGAGTACATATCTCAGAGCTGGTGGAAAGAAGCCAGGGCCTCACCATG

ATCTGTGTCTGGACGGCAGCTCCACTGAGGCCAAGGGCTTAGGAGCCTCC

ATTTCACAGTACATGTGGACCGACATCACAGTGGCATTGTCTAGCTTGAG

CCAATCACAGCTCTGGTCCAGAGCCAATTGGGACCTTGTGGCTACCTTAC

CCTTTGCCTTGCCCTCTGAAGGTGAGTGGTAGGGTGGCCTCAACTCAGGA

GTAGTCTATGGATTCTCTTGCTTGCCTTGGTTGTGGCTGACAGCTGAGCC

CAAGCTTCTAGGGACTGGTTCCCAAGGCCAGTAGGATCCCAGGGATTGTA

GCCTCCTCCATTGACTGGGTGGTCAGTTTAGATGTTGGTCCTGCTCCACA

AACATCCCTTCACCAAGAATTAAGCCCAATAGCAAGAGCCACATTCTTTG

AAAGAGACCAGAGGCTTTTCAGTTTAACTTAAAGGCCTTTGGGGACTGGG

CAGTGGTAGTGCAAGCAAAGCCTTTAATCCTAGCACAAACGAGACAGAGG

TAGTTGTATCTGTGATTTTGAGGCCAGCCTGATCTACAGAGTGAGTTCTA
```

-continued

```
GGACAGCTAGAGCTGTTTCACAGAGAAACCCTGTCTGGAAGAAATAAAAC

AAAAGGCCTTGGAGAGATAAGCTTTAGAATACATGCTTTAGTGTAGTTCT

TTTTGTGTATAACATGGTTTCCATATTGGCATAGAGATCACACTGGGCAG

ATAACCATATTAACTGAGCAGAAAGAATATAAAGTAGGCCTAAGGGAACA

TTAGTGGAGCTACTGACAATCCTCTCCTTCAGCTGCAATCTATTTTGGGA

GATGCCTGAGTATACACAAAGTAAAAGGGCCACTCCATGATTAAGTGTCC

AGGTCATAATCCTCGATTGGGTAGGACTGTTTGCTGTTTCAGGGCCACAC

ACGCTCAATAACGCTTCATGAAGTTGAACTTGAGTGGAATCATACTTTGG

CCATCACTAGTGCACTATTTGGGGTGAACAGATGTCTTCCCTAGAAGGGG

AAATGCCAACACACTACTTCTAGGTGGTCATGTAAAAATTTTTGAAATAG

ACCGGGCATTGGTGGCACACACCTTTATTCCTACCACTCAGGAGGCAGAG

GCAGGTGGATCTCTGTGAATTTGCAATCAGCCTGGTCTACAAGCCCTAGT

TGCAAGGCAGCCTCCAAAGTCACAGAGAAACCCTGTCTTGAACGCACCCC

CCCCCCCCCCCCCGCCCAATTTTTTTTTTTAAAATAACCTGGCTGGAG

AGATGGCTCAGAAGTTAAGAGCACTGACTGCCCTTCCGGAGGTCCTGAGT

TCAATTCCAGGCAACCTTATGGTGGCTCAAAACCATCTGTAATGAGATTT

GGCGCCCTCTTCTGGCATGCAACATACATGTTGGTAGCACACTGTATATA

TAATAAATAAATCTTGTCTCTGACTCTCAGTGCAAGCAACCACACCCAAG

CTCCAGTCATTTAAAGAAGCCAAACACTGAAACCAATGGGAGCTCCTGTA

GCATCCTTGTTCTGCTGCTTGATGATCACTCTGGATGAGGAATACCTGTG

TGGTGCACAGTACATCTGGAGCATGAGTACAAGACAAGGCCTAACCCAGA

TGAAACTTGTCACATACACATTTCTACCTGTGTAGTGACATTTGGAAGGC

CGAAGCAGGATTGTTAAATTCCATGTCCTCACTGAATACACAGCAGGACC

CACTCTCAAAACAAAACAAAACTTAGGGTTCAACTATACGAAACTCCAGT

TCCAGGGGCTCAGATATCTTTTTACGGCCACAGGCATCAGACAACGTGGT

GCATATACATTCATGCAGGCAAAATAAAAGCGCACTTAAAGAAAAGCTGG

AATCTAGCAGGGTGGAATCTAACTTACAGGGGTCTGGCTGCGTCGGCCAT

CCAGATGCTACCTGTTGGGACTAACACACCCGCCACGAATACGTTTTTCA

CCTAGATTGACAGAAACCCTCCAAGAAAACAGAAGAAAAACACAAACAA

AACACCACCACCACATACACGGTAGGTTATGTTAAACCACTTTATTT

GAGAAGAGGACATCGGAACCCTGCCATTTTCGTGGGCGAAGCTGCAGCCG

CCTCCAGATCCAGTGGAACCTGTGGATAAAGGACATGGTTAGGATCGATG

CCACACACAAGCCAGGCCGCGGGAGCCGCGAGGCGGTCGGGAATGTAGGG

GCCTGGGTTTCACCCTCCCACACTGGGGCAGCGGCGGTGAGCTGAGGCC

CCTGTGGCTCTGGGCGCCGAATCTCACCTCCGGCCACAGCCAAGGCCGAA

AATGATTTTCAACGAACGCCCATTTACCGAGCCCACGGCGAACGCGAGGC

TGACGAGGTACAACCTACCTGAGGCAGAGAGAAAGAGCAGGAAGTGACGA

GCACTAGGAGGCCTGAGAGGCGCCACCCGGACTTTTATACACCCTCACAG

TCGGCGTACGTCGCGGCTTCGGCGAGGCGATATGCGCAGGCGCAGATGGA

ACGTGCGGGCGGGGGGGGGAGGTGACAACACGCAGCCAATTACAGCC
```

-continued

```
TGCGTGTGAGCTGAGCAGGCCTGGAGATATCGCGGCGCTAGGGGCACTAT

AAAGTCTGCCTTCCCCACAGCCGCGCTCTTCTTCTACTTCGGGAAAACAC

GTGAGTCGTTGTTCCTCAGTCCCGGTGTCGGGGCCTGGGCAGTGGGAATC

CGTGGACATCCGGACGGAGACGCCCTTGGGCGGGAGGTCCCCTATCGGAA

TCCCAAGCGACCGCAAAGCCAATTGTCGTTCTGAGTTGCTTTTTTGCTTC

TCTAGCAAATGGCGGATGACGCCGGTGCAGCTGGAGGGCCCGGAGGACCC

GGGGGCCCAGGATTAGGAGGTCGCGGAGGCTTCCGCGGAGGCTTTGGCAG

CGGTCTCA//.
```

Construction of pPT4 and pPT4.1 Vectors.

The hamster Rps2 genomic element was introduced within pPT3 in either plus (pPT4) or minus (pPT4.1) orientation (FIG. 8). In the plus orientation, Rps2 was amplified using forward primer 5'-GGA ATT AGA CGG ATC CCA AAG AGG TTG AGA TCG TAC C-3'//SEQ ID NO:39 and reverse primer 5'-CGT AAG TTA TGT AAC GGA TCC TGA GAC CGC TGC CAA AGC-3'//SEQ ID NO:40. In the minus orientation, we used forward primer 5'-GGA ATT AGA CGG ATC CTG AGA CCG CTG CCA AAG C-3'//SEQ ID NO:41 and reverse primer 5'-CGT AAG TTA TGT AAC GGA TCC CAA AGA GGT TGA GAT CGT ACC-3'//SEQ ID NO:42. To shuttle the PCR products into pPT3, we used restriction enzymes PvuI and BamHI, necessitating the replacement of part of the Ampicillin Resistance gene and the replication Ori. This was provided by a PCR product using forward primer 5'-CAA CTT ACT TCT GAC AAC GAT CG-37/SEQ ID NO:43 and reverse primer 5'-GGA TCC GTC TAA TTC CGG TCT CCC TAT AG-3'//SEQ ID NO:44. All fragments were assembled using SLIC methodology.

The hamster Rps3 genomic element was introduced within pPT3 in either plus (pPT4.2) or minus (pPT4.3) orientation. In the plus orientation, Rps3 was amplified using forward primer 5'-GGA ATT AGA CGG ATC CGA TTA GAA GCC ATC TTG TTA CAA A-3'//SEQ ID NO:45 and reverse primer 5'-CGT AAG TTA TGT AAC GGA TCC TAT ATA ACT CTG AAA GTG TCA ACC C-3'//SEQ ID NO:46. In the minus orientation, we used forward primer 5'-GGA ATT AGA CGG ATC CTA TAT AAC TCT GAA AGT GTC AAC CCA-3'//SEQ ID NO:47 and reverse primer 5'-CGT AAG TTA TGT AAC GGA TCC GAT TAG AAG CCA TCT TGT TAC AAA-3'//SEQ ID NO:48. These fragments were then assembled using the same methodology used for the Rps2 containing constructs.

The new pPT4.x vectors (FIG. 8) along with appropriate controls were transfected into CHO-S cells and selected with puromycin. Once the pools were recovered, 4-mL batch productions were set up after the initial recovery of the pools and 2 weeks, 1 month and 2 months after recovery. For each batch production, samples were collected and the conditioned media (CM) from these batch productions was used to determine titer by ForteBio OCTET® Red, as in Example 2.

Results:

In order to increase the stability of expression in CHO pools, we looked for hamster genomic elements which may have regulator function to prevent silencing by epigenetic mechanisms. We sought out regulatory sequences which are associated with hamster genes that have high expression levels in our CHO lines. Mining of RNA sequence data from CHO expressed genes showed Rsp2 and Rsp3 genes fit this criterion. Human Rsp2 has been previously shown to confer stabilizing properties to vectors containing CMV promoters (Williams S et al. CpG Island fragments from HNRAP2B1/CBX3 genomic locus reduce silencing and enhance transgene expression from the hCMV promoter/enhance in mammalian cells. BMC Biotechnol. 5:17 (2005)). As shown in FIG. 9, inclusion of the hamster Rps2 and Rps3 gene sequences conferred stability on the CHO-S transfected pools over a 2 month period. The GAPDH promoter elicited high expression levels throughout the experiment and outperformed the pPT2 vector for both exogenous gene titer and stability. The pPT2 series vectors, without the Rps elements also lost expression over two months. However, when the hamster Rps2 or Rps3 elements in the plus orientation greater stability was conferred to the vector; whereas the expression profile was similar to the expression profile for vectors with no element at all, when the hamster Rps2 or Rps3 elements were added to the expression vector in the minus orientation.

What is claimed:

1. A recombinant expression vector, comprising an expression cassette comprising a hamster GAPDH promoter, operably linked to an exogenous gene of interest, further comprising a regulatory element that
   (a) comprises a nucleic acid sequence that is at least 95% identical to the nucleic acid sequence set forth in SEQ ID NO:35 or to the nucleic acid sequence set forth in SEQ ID NO:38; and
   (b) is operably linked to the promoter.

2. The recombinant expression vector of claim 1, wherein the GAPDH promoter comprises the nucleotide sequence of SEQ ID NO:50.

3. The recombinant expression vector of claim 1, comprising, 3' to the GAPDH promoter and 5' to the gene of interest, the nucleotide sequence of SEQ ID NO:52.

4. The recombinant expression vector of claim 1, wherein the regulatory element comprises a nucleic acid sequence at least 98% identical to SEQ ID NO:35 or to SEQ ID NO:38.

5. The recombinant expression vector of claim 1, wherein the regulatory element comprises a nucleic acid sequence at least 99% identical to SEQ ID NO:35 or to SEQ ID NO:38.

6. The recombinant expression vector of claim 1, wherein the regulatory element comprises the nucleic acid sequence of SEQ ID NO:35.

7. The recombinant expression vector of claim 1, wherein the regulatory element comprises the nucleic acid sequence of SEQ ID NO:38.

8. The recombinant expression vector of claim 1, wherein the regulatory element is in the plus orientation.

9. An isolated mammalian host cell comprising the recombinant expression vector of claim 1.

10. The mammalian host cell of claim 9, wherein the cell is a Chinese Hamster Ovary (CHO) cell.

* * * * *

SEQUENCE LISTING

```
<160> NUMBER OF SEQ ID NOS: 54

<210> SEQ ID NO 1

<400> SEQUENCE: 1

000

<210> SEQ ID NO 2

<400> SEQUENCE: 2

000

<210> SEQ ID NO 3

<400> SEQUENCE: 3

000

<210> SEQ ID NO 4

<400> SEQUENCE: 4

000

<210> SEQ ID NO 5

<400> SEQUENCE: 5

000

<210> SEQ ID NO 6

<400> SEQUENCE: 6

000

<210> SEQ ID NO 7

<400> SEQUENCE: 7

000

<210> SEQ ID NO 8

<400> SEQUENCE: 8

000

<210> SEQ ID NO 9
<211> LENGTH: 29
<212> TYPE: DNA
<213> ORGANISM: ARTIFICIAL SEQUENCE
<220> FEATURE:
<223> OTHER INFORMATION: Forward Primer

<400> SEQUENCE: 9
```
ctacccagag acctatttct gtcatagcc    29

<210> SEQ ID NO 10
<211> LENGTH: 19
<212> TYPE: DNA
<213> ORGANISM: ARTIFICIAL SEQUENCE
<220> FEATURE:
<223> OTHER INFORMATION: Reverse Primer

<400> SEQUENCE: 10
ccaggcgtcc aatacggcc    19

<210> SEQ ID NO 11
<211> LENGTH: 4210
<212> TYPE: DNA
<213> ORGANISM: Cricetulus griseus
<220> FEATURE:
<221> NAME/KEY: misc_feature
<223> OTHER INFORMATION: Chinese hamster GAPDH gene, -2049 through +2161
      relative to transcription start site

<400> SEQUENCE: 11
ctacccagag acctatttct gtcatagcct tttgggacac ataaagcttc cttcctgcat    60
agaacacccc acaacagtgt atcaggagtg tacaagttga caaacaatgc tctagaccta   120
cggttttctt cctctgtgtg cctcatccca gaagagatca tgactcccag gagtcagcct   180
ttactatggg gtctgcaggg gcgtccagcc cctcagcggc aagccatgcc caccctcccc   240
aagtccttaa tctgctgagt cacttggaac aggagacact gattctgctg tcatgacaac   300
agcacattgc catagaaatg ctccctacct cttacgtgtg tggtggggga acagtaatga   360
caaaccatag gcaggaggca aaagggaaga cggcacctca gaaacatgtg ttaggttagg   420
gcagaactat ggaggggctc ctgagactct tgatgggaa agggttaatg ctgctcctga   480
aacctctgtt ggaaggcaga aaagggacag ggctgagtcc ccgcactggg accatttcca   540
tcctctgcat cctgccccg gctcatggaa agcctgggca tgggccacac agctgtcagt    600
cttggctctg ggcccccaag gaggtagggc aatcccagaa tggcaaggag ccaggactgg   660
atttggggtg cagcccagcc tgctccctgc cttttaagca aaggttatca ccaggccagc   720
taaacttagc aattaggctc ttcagctaaa agagcagggg gctggtctca agttgcactg   780
acctagcaaa gaggccccag gatcccctg cccagcacct gtggctgagc tcccaagccc     840
ttcccgagag ctcaggatcc accctttcca ccctccctac tcttcagagg aggaaccccc   900
tttctccttc ccacttgttg gagggggctg gggccaggct gttctggctt ggggtataat   960
acccccctacc ccttctactt tcccctcctc tcagacctca ccctgcctcc acgagggcag 1020
ccaagaaagg agagtccctg gctgcagggc cagtaggcac gtcccaggac ggggagggac 1080
ttccgccctc acgtccagct ctccgccctg gggctgcagt gggtgaaagg ggcagtgtct 1140
cctagcctgg gcggtgcaac cctcaggttc cgaggaggaa cgctctggga ggcttctttg 1200
cctcctccaa cccaacccac aaccaggaca ttgtcctcac cccggggccc caacctagac 1260
cttaactgag gaacacagag gccagttttgt aagtctcaat tatgcagggc atcccgacct 1320
gtggcgtagg gagcgcccct ccaggccgct tccctagcct cctcctggcc ctcacagccc 1380
aggcctctgg cccaagaaat ggaagtgggg gtggggatg gaactgcgaa tgcgaagggc 1440
ccccgcagga ggcaaagtga cccctccgg gccttttctg ctccgagact tgttttgcc   1500
tgtgtcacta ccgaagaacc acgagaagat cctcaacttt tccacagcct ttgcataaag 1560

-continued

```
gggagagggt cggcggtgca gctgtggcac acacgcactt ctgctcaacc cgccccccccc    1620
cgccccccgtt cctgttcctt cccaggttct ccccattttta tcggggcggc aacttttagg    1680
tccctgggtc ctggaagtcc ttagtacaca ctcttcgtcc ttaagtccat agtctgtatt    1740
ccctcggtcc tatcctgtcc cccatcaccg ggtcacctcc ccagcgaagc aatctcagtt    1800
cccctccccc tctcagcccc gagcccacac gtttggtgcg tgcacatttc aaaaacgagg    1860
cgggtccaaa gagagggggt ggggaggtgc cgagtggccc agctactcgc ggctttacgg    1920
gtgcacgtag ctcaggcctc agcgcccttg agctgtgact ggatggatga gcggggcggg    1980
aggcggggcg agcgtcctcg cgctccccca ccaccccagt tcctataaat acggactgca    2040
gccctccccg gtgctctctg ctcctccctg ttctagagac agccgcatct ttccgtgcag    2100
tgccaggtga aaaccgcaga gtgggccgca ggtggccggg gacggtcgga aacggggaag    2160
gggggcgctc agcccgggac tgcgggcgct ggggcgagct ccactgcccg agcccgggct    2220
ccgcattgca gaggctggag ggggacgtga tggggcgcgc ggcgggaatg gaggcggggg    2280
gggggggtcgc cctgtgaccg tggtccacgc tgacctctct ttcttctctc tccctccgca    2340
gcctcgctcc ggagacgcaa tggtgaaggt cggcgtgaac gggtgagttc gtggctgggc    2400
tagggtgggg ctccgggtcc cgctccgtcg cgtatgcagg tctaccccac cccgggggctc    2460
tgcgggagcg tggggtggcc ggtgggtggc cgcagcaccc aaggagacct caaggtcagc    2520
gagccggctc cgcccttgcg gggatgagca gcgcggagtc ctcacgagga ggaccatccc    2580
ccgcgcgcac gcatgcttag gctccatccc gatccccagc cgggggcttc tttctttact    2640
ttcgcgccct gaggaaccac gtgccagacg ggagcccctc ccccattgcc ctctaccccc    2700
cccccccgcgc gcgcctccag gtcggtggca ccgggccgtg cggtgcccgc tttagcgcat    2760
ccatcatctc ccaagggctt cctttagggt ggctggccgc cgccatgttg caaacgggaa    2820
ggaaatgaat gaaccaccgt taggaaacct cccttcggcc ttcctccttc ctagcccgtg    2880
actaacctcc ccactccctc cccgggtgga gtcgcctctg tactgtaagc caggtgatgc    2940
aaggcttccg tgctctcgag agagctctac ctcgccagct gtctcatatt attagcctca    3000
aagcagccct caagcctcat ttaccttgag catatgatat attttgtaga ttctctgaga    3060
atcgaagcgg acttggagag gtctgcttgt ccttctccca gcccaaaggt ggtagctatg    3120
gcgtagcgcc ggaggggggga gtggggggggg agctgagtca tggtggttct gaaaagaaaa    3180
tttccaccac aaaatggctc cggtgctagc atccccttcc ccccataacc tctgcttccc    3240
atcacaccct gacccaaacc ctgtaggcca gactgtaaag gtcactaaga ggattgagtg    3300
tctgagcctc ggaaccctgc ccttctcccc atcccatcct ctggaaacca gatctccccc    3360
gctccaccct aatctgaggt tatatttagc cggctgacct ttcagtattt ggggtctggg    3420
cccctacaca catctgttgc tcctgctcct gattttttagc tagcaaattc aagtgctttg    3480
caaattagag cccagggatt aggggttgga aagctcagtg gttttctcag tctttccctt    3540
taggggagg gacttggagg aagcaggtgg gccgacccct gtcctactca ttctgacctt    3600
taaccttgcc ctttgagctt gatgatgctg agtgcacgag ttcttcctgt ccaggggggtg    3660
tagcctgaag ccaggccagg ctagaacaaa cttcccaggg ggtgggggta gtgaatgcct    3720
tgtgcccaca caggggcaca ctgccacctc ttggagactt gaaatgactg gtgggggggt    3780
tggacaaggc tttgagccca atcacctctt ggacaggaaa gtaaccccca ctttatggcc    3840
ctgctgtaaa agcccagtca aacctcattt gtccaaggaa gatagacctc ttggggcttc    3900
ctaaggatag gggtgttcta tatttgggcc ctgcttctaa gcattcagcc agcttttatta    3960
```

```
aaggaaattc ataacaaaac ttgaatttcc tgcttcttaa atactaatag tgtgctggat    4020
ctccattaaa aatgctgtct tgcacagtag gctatggttt ctgtgggctc tctacagcta    4080
tgggacaact ggattctgtt ttctgaaggg catgtgtcag ctcagtactg actatagacc    4140
tatgagttct ctgaccccct aactcacctt ttttttttctt gcctcagatt tggccgtatt    4200
ggacgcctgg                                                          4210
```

<210> SEQ ID NO 12
<211> LENGTH: 24
<212> TYPE: DNA
<213> ORGANISM: ARTIFICIAL SEQUENCE
<220> FEATURE:
<223> OTHER INFORMATION: Forward Primer 4

<400> SEQUENCE: 12

```
gatagttggc atttgctgtt ctag                                            24
```

<210> SEQ ID NO 13
<211> LENGTH: 38
<212> TYPE: DNA
<213> ORGANISM: ARTIFICIAL SEQUENCE
<220> FEATURE:
<223> OTHER INFORMATION: Reverse Primer 4

<400> SEQUENCE: 13

```
tgtaacggat ccagacttca acacatctat ttttctac                             38
```

<210> SEQ ID NO 14
<211> LENGTH: 38
<212> TYPE: DNA
<213> ORGANISM: ARTIFICIAL SEQUENCE
<220> FEATURE:
<223> OTHER INFORMATION: Forward Primer 5

<400> SEQUENCE: 14

```
tgaagtctgg atccgttaca taacttacgg taaatggc                             38
```

<210> SEQ ID NO 15
<211> LENGTH: 25
<212> TYPE: DNA
<213> ORGANISM: ARTIFICIAL SEQUENCE
<220> FEATURE:
<223> OTHER INFORMATION: Reverse Primer 5

<400> SEQUENCE: 15

```
ccatggtaat agcgatgact aatac                                           25
```

<210> SEQ ID NO 16
<211> LENGTH: 46
<212> TYPE: DNA
<213> ORGANISM: ARTIFICIAL SEQUENCE
<220> FEATURE:
<223> OTHER INFORMATION: Forward Primer 6

<400> SEQUENCE: 16

```
gtcatcgcta ttaccatggc ctcgagacca cgagaagatc ctcaac                    46
```

<210> SEQ ID NO 17
<211> LENGTH: 45
<212> TYPE: DNA
<213> ORGANISM: ARTIFICIAL SEQUENCE
<220> FEATURE:
<223> OTHER INFORMATION: Reverse Primer 6

<400> SEQUENCE: 17
cattccatgg tggcctagtc gacgctagcc tccggagcga ggctg    45

<210> SEQ ID NO 18
<211> LENGTH: 33
<212> TYPE: DNA
<213> ORGANISM: ARTIFICIAL SEQUENCE
<220> FEATURE:
<223> OTHER INFORMATION: Reverse Primer 7

<400> SEQUENCE: 18
cgagctctgc ttatatagga actggggtgg tgg    33

<210> SEQ ID NO 19
<211> LENGTH: 32
<212> TYPE: DNA
<213> ORGANISM: ARTIFICIAL SEQUENCE
<220> FEATURE:
<223> OTHER INFORMATION: Forward Primer 7

<400> SEQUENCE: 19
gttcctatat aagcagagct cgtttagtga ac    32

<210> SEQ ID NO 20
<211> LENGTH: 47
<212> TYPE: DNA
<213> ORGANISM: ARTIFICIAL SEQUENCE
<220> FEATURE:
<223> OTHER INFORMATION: Reverse Primer 8

<400> SEQUENCE: 20
cattccatgg tggcctagtc gacgctagca ggttttccga tccggtc    47

<210> SEQ ID NO 21
<211> LENGTH: 27
<212> TYPE: DNA
<213> ORGANISM: ARTIFICIAL SEQUENCE
<220> FEATURE:
<223> OTHER INFORMATION: Reverse Primer 9

<400> SEQUENCE: 21
cggtactcac cccaacagct ggccctc    27

<210> SEQ ID NO 22
<211> LENGTH: 29
<212> TYPE: DNA
<213> ORGANISM: ARTIFICIAL SEQUENCE
<220> FEATURE:
<223> OTHER INFORMATION: Forward Primer 8

<400> SEQUENCE: 22
ctgttggggt gagtaccgca gagtgggcc    29

<210> SEQ ID NO 23
<211> LENGTH: 26
<212> TYPE: DNA
<213> ORGANISM: ARTIFICIAL SEQUENCE
<220> FEATURE:
<223> OTHER INFORMATION: Reverse Primer 10

<400> SEQUENCE: 23
ccgcgagctg cggagggaga gagaag    26

<210> SEQ ID NO 24
<211> LENGTH: 28

<210> SEQ ID NO 24
<211> LENGTH: 28
<212> TYPE: DNA
<213> ORGANISM: ARTIFICIAL SEQUENCE
<220> FEATURE:
<223> OTHER INFORMATION: Forward Primer 9

<400> SEQUENCE: 24
cctccgcagc tcgcggttga ggacaaac                             28

<210> SEQ ID NO 25
<211> LENGTH: 29
<212> TYPE: DNA
<213> ORGANISM: ARTIFICIAL SEQUENCE
<220> FEATURE:
<223> OTHER INFORMATION: Reverse Primer 11

<400> SEQUENCE: 25
gaactcacct gaggttttcc gatccggtc                            29

<210> SEQ ID NO 26
<211> LENGTH: 28
<212> TYPE: DNA
<213> ORGANISM: ARTIFICIAL SEQUENCE
<220> FEATURE:
<223> OTHER INFORMATION: Forward Primer 10

<400> SEQUENCE: 26
cggaaaacct caggtgagtt cgtggctg                             28

<210> SEQ ID NO 27
<211> LENGTH: 47
<212> TYPE: DNA
<213> ORGANISM: ARTIFICIAL SEQUENCE
<220> FEATURE:
<223> OTHER INFORMATION: Reverse Primer 12

<400> SEQUENCE: 27
cattccatgg tggcctagtc gacgctagcc aaatctgagg caagaaa         47

<210> SEQ ID NO 28
<211> LENGTH: 21
<212> TYPE: DNA
<213> ORGANISM: ARTIFICIAL SEQUENCE
<220> FEATURE:
<223> OTHER INFORMATION: Forward Primer 11

<400> SEQUENCE: 28
gatgtgttga agtctggatc c                                    21

<210> SEQ ID NO 29
<211> LENGTH: 27
<212> TYPE: DNA
<213> ORGANISM: ARTIFICIAL SEQUENCE
<220> FEATURE:
<223> OTHER INFORMATION: Reverse Primer 13

<400> SEQUENCE: 29
caaccgcgag cccaacagct ggccctc                              27

<210> SEQ ID NO 30
<211> LENGTH: 30
<212> TYPE: DNA
<213> ORGANISM: ARTIFICIAL SEQUENCE
<220> FEATURE:
<223> OTHER INFORMATION: Forward Primer 12

<400> SEQUENCE: 30

```
gctgttgggc tcgcggttga ggacaaactc                                    30
```

<210> SEQ ID NO 31

<400> SEQUENCE: 31

000

<210> SEQ ID NO 32

<400> SEQUENCE: 32

000

<210> SEQ ID NO 33
<211> LENGTH: 23
<212> TYPE: DNA
<213> ORGANISM: ARTIFICIAL SEQUENCE
<220> FEATURE:
<223> OTHER INFORMATION: Forward Primer

<400> SEQUENCE: 33

```
gattagaagc catcttgtta caa                                           23
```

<210> SEQ ID NO 34
<211> LENGTH: 25
<212> TYPE: DNA
<213> ORGANISM: ARTIFICIAL SEQUENCE
<220> FEATURE:
<223> OTHER INFORMATION: Reverse Primer

<400> SEQUENCE: 34

```
tatataactc tgaaagtgtc aaccc                                         25
```

<210> SEQ ID NO 35
<211> LENGTH: 3045
<212> TYPE: DNA
<213> ORGANISM: Cricetulus griseus
<220> FEATURE:
<221> NAME/KEY: misc_feature
<223> OTHER INFORMATION: Rps3 genomic fragment

<400> SEQUENCE: 35

```
gattagaagc catcttgtta caaatgtcaa aagatcattc ctgttttctg taatacttgt    60
gtttgaccat gtcttgatcc atcttctgga atttgacatg ttccacacct tataccctga   120
cctccatcct gacaagataa gatgttctgc cactgtccta cataaccaaa atgcctcttc   180
aaatcgccca atccttgaaa tttctgagct atataaattc tactttcttc tatgtccaat   240
gctgtttttt caaactccac tttagggaga caaccctgtt tgacagaaaa taaaacttcc   300
ttaatctaac taaacaatt tgggtaatgg gctttacttt tatttggtgg gatttgcaca    360
gggtgaattg gagcccctg gagatgactg agccacgaac actgtagtac aagttactga    420
agcaggattt gcttctggac aaggagtgat tgctggtgta gacatcggag tccctgtgaa   480
gggatgtcct gtggcccaga cttacacttt ctgataatct gtcttcaaag ccctgctagt   540
ttattacatt gacagctccc ttctggtagc ccaccccact gtgagttcaa aaagttcaga   600
ggtcctggtg caagtgtttg ataccagaaa tgctacaggt aagtccatct ttaggatcag   660
ggtttatctt tgtaataaac atcataggat tgtaatgttt taacaatgac gtgtgtgtgt   720
gtgtgtgtgt gtgtgtgtgt gtgtgtgtgt ttgtgtttgt gtggggagag              780
catgcatggg aaggtcctag gacctaggtt ctgtcctttg acctctgggt gctgggatcg   840
```

| | |
|---|---|
| aaatcaaaca cctttaccta ctaagtcacc tggctggtcc cccaaatgaa tttcaatgag | 900 |
| agttttcatt agtgtggtcc tgaagctata agcaataggg ttccagtctg ggtaaactct | 960 |
| gttagtgtat gctatgtct gtggtttgca tctcttgcct cttggttgct ctgttcaaag | 1020 |
| ttttttattta ttttttgagtc gggggctcat gtagaccaag ctggcttcga actcgctatg | 1080 |
| tagtcgagaa tgaccttgaa tttttgattc tccagcctcc acctctctag tgctgaaatc | 1140 |
| actggtgtgc cctccacgg tggggtacat tgattgtttt tcagaccaga attagatttg | 1200 |
| cacttcctgt tccgcctaca ctacggttg ctaggttaca cttcttttc tcttttcgcc | 1260 |
| tttataaact caaaacttca tttcccatga gctcttgcaa gtgtcgccgt tgcgtggcgt | 1320 |
| tgcgtcgtcg ttccgcgccc tttatacaca cttccgcccg cgagctactt cctttccttt | 1380 |
| cggtggcgcg cggcggcaag atggcggtgc agatttccaa gaagaggaag gtaagcattt | 1440 |
| cggaccggct cggggactcg cggcgcgttt taaagctgcc acggtgagac ccgcagctcc | 1500 |
| gtgtccgatc ccggagagcg gctactgccc cctggcgctt ccgcggggcg cggatggacg | 1560 |
| tggattgtgt gctgggccgg ctccgggcta gctcagtgtg gctgaggaag ggaggaacag | 1620 |
| acgcctcagt tctgggccga ggtgaacact ggaagccatc aggcctttac tagacgcttt | 1680 |
| tgagcgtctc tcggtcgcca gaattagtaa ccctatggca tagcttgaga gcgtgagcta | 1740 |
| atccggcgtc tttggtaagt gaggtttagc agtgccgcct cagttgaaag gctgccgact | 1800 |
| attggcgtgc tccctcggga cctgcagcaa aagcgtcccg gacttttgtc atttcatggg | 1860 |
| gaagaagtgt gtgaagatca tcaggtttag aaatagatgg cctgtctttg tgatcaagca | 1920 |
| catagatcat aaagctgttg tccacatgct gtttgggtta gatttgtcct ctcttgcttc | 1980 |
| aggtacgagt tacatacaca cacggtgttc ttgctgtgct gtgtgaactg cagatgtgct | 2040 |
| acttgaatag atttttgttc tgtgtgtgta aatgttttaa aacccttcga tgaagaggtg | 2100 |
| atgacgagtc tgacggaggt gttgtctttg tccaaaaggc gtcactgtgc tgcgttctgt | 2160 |
| ggcacagctg aaagcactat ggtcaaagga acttcctaaa gatgacctag aggcatttgt | 2220 |
| ctgagaaggg ttgctgcatt cccgaagggt cattgggtc gaactgggta agcctctacc | 2280 |
| cttctttaac tctgaacttg cttttggttt agtttgtggc tgatggcatc ttcaaagcag | 2340 |
| agctgaatga gtttctcact cgggaactgg ctgaagacgg ctactcggga gttgaagtcc | 2400 |
| gagttacacc aaccagaaca gaaatcatta ttttagccac caggtaaaaa tatgtttgac | 2460 |
| tggctattac ctgtaatcac tgtgtgtatt gagttgctgt gtaaacttgg aacaaccaac | 2520 |
| cagtgaacct gctcctttt tgttgttgtt ttttgtttgt tttttgagac agggtttctc | 2580 |
| tgcattgctt gggagcctgg cctggaactt gctctgtgga tcagtctggc ctaagactca | 2640 |
| cagagatccg cctgctctgc ctcctgagtg ctgggattaa aggtgtgcac caccaccact | 2700 |
| gcctggcctt ggagttgctt ttttaaaaca ccatttgtaa agaatttacc ttaatacttt | 2760 |
| tttaaagtgt gtccttgctg tgtgataaat ggtatgtgag gtgttgcaaa taaattgtaa | 2820 |
| ttttcccttc tgcagaacac aaaatgttct tggtgagaag ggtcgtcgaa tcagagagtt | 2880 |
| gactgcggta gttcagaaga ggttcggctt ccctgagggc agcgtagagg tgagtttccc | 2940 |
| tggtttatac caggggcagt agactggatt tagaagttgc ttctgtagaa cggtaattct | 3000 |
| ggacaatgag tagtacaggt gggttgacac tttcagagtt atata | 3045 |

<210> SEQ ID NO 36
<211> LENGTH: 22
<212> TYPE: DNA
<213> ORGANISM: ARTIFICIAL SEQUENCE

<220> FEATURE:
<223> OTHER INFORMATION: Forward Primer

<400> SEQUENCE: 36
caaagaggtt gagatcgtac cc                                             22

<210> SEQ ID NO 37
<211> LENGTH: 18
<212> TYPE: DNA
<213> ORGANISM: ARTIFICIAL SEQUENCE
<220> FEATURE:
<223> OTHER INFORMATION: Reverse Primer

<400> SEQUENCE: 37
tgagaccgct gccaaagc                                                  18

<210> SEQ ID NO 38
<211> LENGTH: 3258
<212> TYPE: DNA
<213> ORGANISM: Cricetulus griseus
<220> FEATURE:
<221> NAME/KEY: misc_feature
<223> OTHER INFORMATION: Rps2 genomic fragment

<400> SEQUENCE: 38
caaagaggtt gagatcgtac ccaccactct gcaaaggcca agttagtgtt aaagtctgtc      60
ccaaagcaca cataccatca agataactcc ataatcattc gtagggagg caggctacat      120 aaagaaactc aagggcaaac ctgtgggggt tgagtcccc aagatttgcc aatatttgac      180
tgaagaagct ggaataccac ctagagcctt ctgaaatgtt ttcttgcccc ataaaggaac      240
tatcattcat tcgcagagtg agacaggatc gattcctaga cagctgggca gctgtctgga      300
attgagtaca tatctcagag ctggtggaaa gaagccaggg cctcaccatg atctgtgtct      360
ggacggcagc tccactgagg ccaagggctt aggagcctcc atttcacagt acatgtggac      420
cgacatcaca gtggcattgt ctagcttgag ccaatcacag ctctggtcca gagccaattg      480
ggaccttgtg gctaccttac cctttgcctt gccctctgaa ggtgagtggt agggtggcct      540
caactcagga gtagtctatg gattctcttg cttgccttgg ttgtggctga cagctgagcc      600
caagcttcta gggactggtt cccaaggcca gtaggatccc agggattgta gcctcctcca      660
ttgactgggt ggtcagttta gatgttggtc ctgctccaca aacatccctt caccaagaat      720
taagcccaat agcaagagcc acattctttg aaagagacca gaggcttttc agtttaactt      780
aaaggccttt ggggactggg cagtggtagt gcaagcaaag cctttaatcc tagcacaaac      840
gagacagagg tagttgtatc tgtgattttg aggccagcct gatctacaga gtgagttcta      900
ggacagctag agctgtttca cagagaaacc ctgtctggaa gaaataaaac aaaaggcctt      960
ggagagataa gctttagaat acatgcttta gtgtagttct ttttgtgtat aacatggttt     1020
ccatattggc atagagatca cactgggcag ataaccatat taactgagca gaaagaatat     1080
aaagtaggcc taagggaaca ttagtggagc tactgacaat cctctccttc agctgcaatc     1140
tattttggga gatgcctgag tatacacaaa gtaaagggc cactccatga ttaagtgtcc     1200
aggtcataat cctcgattgg gtaggactgt ttgctgtttc agggcacac acgctcaata     1260 acgcttcatg aagttgaact tgagtggaat catactttgg ccatcactag tgcactattt     1320
ggggtgaaca gatgtcttcc ctagaagggg aaatgccaac acactactc taggtggtca     1380 tgtaaaaatt tttgaaatag accgggcatt ggtggcacac accttattc ctaccactca     1440 ggaggcagag gcaggtggat ctctgtgaat ttgcaatcag cctggtctac aagccctagt     1500

-continued

```
tgcaaggcag cctccaaagt cacagagaaa ccctgtcttg aacgcacccc cccccccccc    1560
ccccgcccaa ttttttttt ttaaaataac ctggctggaa gatggctcaa gaagttaaga     1620
gcactgactg cccttccgga ggtcctgagt tcaattccag gcaaccttat ggtggctcaa    1680
aaccatctgt aatgagattt ggcgccctct tctggcatgc aacatacatg ttggtagcac    1740
actgtatata taataaataa atcttgtctc tgactctcag tgcaagcaac cacacccaag    1800
ctccagtcat ttaagaagc caaacactga accaatggg agctcctgta gcatccttgt      1860
tctgctgctt gatgatcact ctggatgagg aatacctgtg tggtgcacag tacatctgga    1920
gcatgagtac aagacaaggc ctaacccaga tgaaacttgt cacatacaca tttctacctg    1980
tgtagtgaca tttggaaggc cgaagcagga ttgttaaatt ccatgtcctc actgaataca    2040
cagcaggacc cactctcaaa acaaaacaaa acttagggtt caactatacg aaactccagt    2100
tccaggggct cagatatctt tttacggcca caggcatcag acaacgtggt gcatatacat    2160
tcatgcaggc aaaataaaag cgcacttaaa gaaaagctgg aatctagcag ggtggaatct    2220
aacttacagg ggtctggctg cgtcggccat ccagatgcta cctgttggga ctaacacacc    2280
cgccacgaat acgttttca cctagattga cagaaaccct ccaagaaaac cagaagaaaa     2340
acacaaacaa aacaccacca ccaccacata cacggtaggt tatgttaaac cactttattt    2400
gagaagagga catcggaacc ctgccatttt cgtgggcgaa gctgcagccg cctccagatc    2460
cagtggaacc tgtggataaa ggacatggtt aggatcgatg ccacacacaa gccaggccgc    2520
gggagccgcg aggcggtcgg gaatgtaggg gcctgggttt caccctccca cactggggca    2580
gcgggcggtg agctgaggcc cctgtggctc tgggcgccga atctcacctc cggccacagc    2640
caaggccgaa aatgattttc aacgaacgcc catttaccga gcccacggcg aacgcgaggc    2700
tgacgaggta caacctacct gaggcagaga gaaagagcag gaagtgacga gcactaggag    2760
gcctgagagg cgccacccgg actttttatac accctcacag tcggcgtacg tcgcggcttc    2820
ggcgaggcga tatgcgcagg cgcagatgga acgtgcgggg cggggggggg ggaggtgaca    2880
acacgcagcc aattacagcc tgcgtgtgag ctgagcaggc ctggagatat cgcggcgcta    2940
ggggcactat aaagtctgcc ttccccacag ccgcgctctt cttctacttc gggaaaacac    3000
gtgagtcgtt gttcctcagt cccggtgtcg gggcctgggc agtgggaatc cgtggacatc    3060
cggacggaga cgcccttggg cgggaggtcc cctatcggaa tcccaagcga ccgcaaagcc    3120
aattgtcgtt ctgagttgct ttttgcttc tctagcaaat ggcggatgac gccggtgcag     3180
ctggagggcc cggaggaccc gggggcccag gattaggagg tcgcggaggc ttccgcggag    3240
gctttggcag cggtctca                                                  3258
```

<210> SEQ ID NO 39
<211> LENGTH: 37
<212> TYPE: DNA
<213> ORGANISM: ARTIFICIAL SEQUENCE
<220> FEATURE:
<223> OTHER INFORMATION: Forward Primer

<400> SEQUENCE: 39
ggaattagac ggatcccaaa gaggttgaga tcgtacc                              37

<210> SEQ ID NO 40
<211> LENGTH: 39
<212> TYPE: DNA
<213> ORGANISM: ARTIFICIAL SEQUENCE
<220> FEATURE:

<223> OTHER INFORMATION: Reverse Primer

<400> SEQUENCE: 40
cgtaagttat gtaacggatc ctgagaccgc tgccaaagc                                      39

<210> SEQ ID NO 41
<211> LENGTH: 34
<212> TYPE: DNA
<213> ORGANISM: ARTIFICIAL SEQUENCE
<220> FEATURE:
<223> OTHER INFORMATION: Forward Primer

<400> SEQUENCE: 41
ggaattagac ggatcctgag accgctgcca aagc                                           34

<210> SEQ ID NO 42
<211> LENGTH: 42
<212> TYPE: DNA
<213> ORGANISM: ARTIFICIAL SEQUENCE
<220> FEATURE:
<223> OTHER INFORMATION: Reverse Primer

<400> SEQUENCE: 42
cgtaagttat gtaacggatc ccaaagaggt tgagatcgta cc                                  42

<210> SEQ ID NO 43
<211> LENGTH: 23
<212> TYPE: DNA
<213> ORGANISM: ARTIFICIAL SEQUENCE
<220> FEATURE:
<223> OTHER INFORMATION: Forward Primer

<400> SEQUENCE: 43
caacttactt ctgacaacga tcg                                                       23

<210> SEQ ID NO 44
<211> LENGTH: 29
<212> TYPE: DNA
<213> ORGANISM: ARTIFICIAL SEQUENCE
<220> FEATURE:
<223> OTHER INFORMATION: Reverse Primer

<400> SEQUENCE: 44
ggatccgtct aattccggtc tccctatag                                                 29

<210> SEQ ID NO 45
<211> LENGTH: 40
<212> TYPE: DNA
<213> ORGANISM: ARTIFICIAL SEQUENCE
<220> FEATURE:
<223> OTHER INFORMATION: Forward Primer

<400> SEQUENCE: 45
ggaattagac ggatccgatt agaagccatc ttgttacaaa                                     40

<210> SEQ ID NO 46
<211> LENGTH: 46
<212> TYPE: DNA
<213> ORGANISM: ARTIFICIAL SEQUENCE
<220> FEATURE:
<223> OTHER INFORMATION: Reverse Primer

<400> SEQUENCE: 46
cgtaagttat gtaacggatc ctatataact ctgaaagtgt caaccc                              46

```
<210> SEQ ID NO 47
<211> LENGTH: 42
<212> TYPE: DNA
<213> ORGANISM: ARTIFICIAL SEQUENCE
<220> FEATURE:
<223> OTHER INFORMATION: Forward Primer

<400> SEQUENCE: 47
ggaattagac ggatcctata taactctgaa agtgtcaacc ca                          42

<210> SEQ ID NO 48
<211> LENGTH: 45
<212> TYPE: DNA
<213> ORGANISM: ARTIFICIAL SEQUENCE
<220> FEATURE:
<223> OTHER INFORMATION: Reverse Primer

<400> SEQUENCE: 48
cgtaagttat gtaacggatc cgattagaag ccatcttgtt acaaa                       45

<210> SEQ ID NO 49
<211> LENGTH: 837
<212> TYPE: DNA
<213> ORGANISM: Cricetulus griseus
<220> FEATURE:
<221> NAME/KEY: misc_feature
<223> OTHER INFORMATION: GAPDH gene fragment (-532 through +305)

<400> SEQUENCE: 49
accacgagaa gatcctcaac ttttccacag cctttgcata aaggggagag ggtcggcggt       60
gcagctgtgg cacacacgca cttctgctca acccgccccc ccccgccccc gttcctgttc      120
cttcccaggt tctccccatt ttatcggggc ggcaactttt aggtccctgg gtcctggaag      180
tccttagtac acactcttcg tccttaagtc catagtctgt attccctcgg tcctatcctg      240
tcccccatca ccgggtcacc tccccagcga agcaatctca gttcccctcc cctctcagc      300 cccgagccca cacgtttggt gcgtgcacat ttcaaaaacg aggcgggtcc aaagagaggg      360
ggtggggagg tgccgagtgg cccagctact cgcggcttta cgggtgcacg tagctcaggc      420
ctcagcgccc ttgagctgtg actggatgga tgagcgggc gggaggcggg gcgagcgtcc       480
tcggcgctcc ccaccacccc agttcctata aatacggact gcagccctcc ccggtgctct      540
ctgctcctcc ctgttctaga gacagccgca tctttccgtg cagtgccagg tgaaaaccgc      600
agagtgggcc gcaggtggcc ggggacggtc ggaaacgggg aaggggggcg ctcagcccgg      660
gactgcgggc gctggggcga gctccactgc ccgagcccgg gctccgcatt gcagaggctg      720 gaggggacg tgatggggcg cgcggcggga atggaggcgg gggggggggt cgccctgtga       780
ccgtggtcca cgctgacctc tctttcttct ctctcccctcc gcagcctcgc tccggag        837

<210> SEQ ID NO 50
<211> LENGTH: 510
<212> TYPE: DNA
<213> ORGANISM: Cricetulus griseus
<220> FEATURE:
<221> NAME/KEY: misc_feature
<223> OTHER INFORMATION: GAPDH promoter (-532 through -23)

<400> SEQUENCE: 50
accacgagaa gatcctcaac ttttccacag cctttgcata aaggggagag ggtcggcggt       60
gcagctgtgg cacacacgca cttctgctca acccgccccc ccccgccccc gttcctgttc      120
cttcccaggt tctccccatt ttatcggggc ggcaactttt aggtccctgg gtcctggaag      180
```

| | |
|---|---|
| tccttagtac acactcttcg tccttaagtc catagtctgt attccctcgg tcctatcctg | 240 |
| tcccccatca ccgggtcacc tccccagcga agcaatctca gttcccctcc ccctctcagc | 300 |
| cccgagccca cacgtttggt gcgtgcacat ttcaaaaacg aggcgggtcc aaagagaggg | 360 |
| ggtggggagg tgccgagtgg cccagctact cgcggcttta cggtgcacg tagctcaggc | 420 |
| ctcagcgccc ttgagctgtg actggatgga tgagcggggc gggaggcggg gcgagcgtcc | 480 |
| tcggcgctcc ccaccacccc agttcctata | 510 |

```
<210> SEQ ID NO 51
<211> LENGTH: 231
<212> TYPE: DNA
<213> ORGANISM: Cricetulus griseus
<220> FEATURE:
<221> NAME/KEY: misc_feature
<223> OTHER INFORMATION: GAPDH intron 1 (+64 through +293)

<400> SEQUENCE: 51
```

| | |
|---|---|
| accgcagagt gggccgcagg tggccgggga cggtcggaaa cggggaaggg gggcgctcag | 60 |
| cccgggactg cgggcgctgg ggcgagctcc actgcccgag cccgggctcc gcattgcaga | 120 |
| ggctggaggg ggacgtgatg gggcgcgcgg cgggaatgga ggcgggggg ggggtcgccc | 180 |
| tgtgaccgtg gtccacgctg acctctcttt cttctctctc cctccgcagc c | 231 |

```
<210> SEQ ID NO 52
<211> LENGTH: 1812
<212> TYPE: DNA
<213> ORGANISM: Cricetulus griseus
<220> FEATURE:
<221> NAME/KEY: misc_feature
<223> OTHER INFORMATION: GAPDH intron 2 (+334 through +2145)

<400> SEQUENCE: 52
```

| | |
|---|---|
| gtgagttcgt ggctgggcta gggtgggget ccgggtcccg ctccgtcgcg tatgcaggtc | 60 |
| taccccaccc cggggctctg cgggagcgtg gggtggccgg tgggtggccg cagcacccaa | 120 |
| ggagacctca aggtcagcga gccggctccg cccttgcggg gatgagcagc gcggagtcct | 180 |
| cacgaggagg accatccccc gcgcgcacgc atgcttaggc tccatcccga tccccagccg | 240 |
| ggggcttctt tctttacttt cgcgcccctga ggaaccacgt gccagacggg agcccctccc | 300 |
| ccattgccct ctaccccccc ccgcgcgc gcctccaggt cggtggcacc gggccgtgcg | 360 |
| gtgcccgctt tagcgcatcc atcatctccc aagggcttcc tttagggtgg ctggccgccg | 420 |
| ccatgttgca aacgggaagg aaatgaatga accaccgtta ggaaacctcc cttcggcctt | 480 |
| cctccttcct agcccgtgac taacctcccc actccctccc cgggtggagt cgcctctgta | 540 |
| ctgtaagcca ggtgatgcaa ggcttccgtg ctctcgagag agctctacct cgccagctgt | 600 |
| ctcatattat tagcctcaaa gcagccctca agcctcattt accttgagca tatgatatat | 660 |
| tttgtagatt ctctgagaat cgaagcggac ttggagaggt ctgcttgtcc ttctcccagc | 720 |
| ccaaaggtgg tagctatggc gtagcgccgg agggggagt gggggggag ctgagtcatg | 780 |
| gtggttctga aaagaaaatt tccaccacaa aatggctccg gtgctagcat ccccttcccc | 840 |
| ccataacctc tgcttcccat cacacccctga cccaaaccct gtaggccaga ctgtaaaggt | 900 |
| cactaagagg attgagtgtc tgagcctcgg aaccctgccc ttctccccat cccatcctct | 960 |
| ggaaaccaga tctcccccgc tccaccctaa tctgaggtta tatttagccg gctgaccttt | 1020 |
| cagtatttgg ggtctgggcc cctacacaca tctgttgctc ctgctcctga ttttttagcta | 1080 |
| gcaaattcaa gtgctttgca aattagagcc cagggattag gggttggaaa gctcagtggt | 1140 |

```
tttctcagtc tttcccttta gggggaggga cttggaggaa gcaggtgggc cgacccctgt    1200
cctactcatt ctgacctttaa accttgccct ttgagcttga tgatgctgag tgcacgagtt    1260
cttcctgtcc aggggtgta gcctgaagcc aggccaggct agaacaaact tcccaggggg     1320
tgggggtagt gaatgccttg tgcccacaca gggcacact gccacctctt ggagacttga    1380
aatgactggt gggggggttg dacaaggctt tgagcccaat cacctcttgg acaggaaagt    1440 aaccccact ttatggccct gctgtaaaag cccagtcaaa cctcatttgt ccaaggaaga    1500
tagacctctt ggggcttcct aaggataggg gtgttctata tttgggccct gcttctaagc    1560
attcagccag ctttattaaa ggaaattcat aacaaaactt gaatttcctg cttcttaaat    1620
actaatagtg tgctggatct ccattaaaaa tgctgtcttg cacagtaggc tatggtttct    1680
gtgggctctc tacagctatg ggacaactgg attctgtttt ctgaagggca tgtgtcagct    1740
cagtactgac tatagaccta tgagttctct gaccccctaa ctcaccttt tttttcttgc    1800 ctcagatttg gc                                                          1812
```

<210> SEQ ID NO 53
<211> LENGTH: 66
<212> TYPE: PRT
<213> ORGANISM: ARTIFICIAL SEQUENCE
<220> FEATURE:
<223> OTHER INFORMATION: VK-1 signal peptide coding sequence

<400> SEQUENCE: 53

```
Ala Thr Gly Gly Ala Cys Ala Thr Gly Ala Gly Gly Thr Gly Cys
 1               5                  10                  15

Cys Cys Gly Cys Thr Cys Ala Gly Cys Thr Cys Cys Thr Gly Gly Gly
            20                  25                  30

Gly Cys Thr Cys Cys Thr Gly Cys Thr Gly Cys Thr Gly Thr Gly Gly
            35                  40                  45

Cys Thr Gly Ala Gly Ala Gly Gly Thr Gly Cys Cys Cys Gly Cys Thr
        50                  55                  60

Gly Thr
65
```

<210> SEQ ID NO 54
<211> LENGTH: 22
<212> TYPE: PRT
<213> ORGANISM: ARTIFICIAL SEQUENCE
<220> FEATURE:
<223> OTHER INFORMATION: VK-1 signal peptide sequence

<400> SEQUENCE: 54

```
Met Asp Met Arg Val Pro Ala Gln Leu Leu Gly Leu Leu Leu Leu Trp
 1               5                  10                  15

Leu Arg Gly Ala Arg Cys
            20
```